(12) United States Patent
Mazzoli et al.

(10) Patent No.: US 9,528,132 B2
(45) Date of Patent: Dec. 27, 2016

(54) RECOMBINANT CELLULOSOME COMPLEX AND USES THEREOF

(71) Applicant: CARBIOS, Saint-Beauzire (FR)

(72) Inventors: Roberto Mazzoli, Turin (IT); Enrica Pessione, Turin (IT); Loredana Tarraran, Pino Torinese (IT); Chiara Gandini, Alessandria (IT)

(73) Assignee: CARBIOS, Saint-Beauzire (FR)

( * ) Notice: Subject to any disclaimer, the term of this patent is extended or adjusted under 35 U.S.C. 154(b) by 0 days.

(21) Appl. No.: 14/405,504

(22) PCT Filed: Jun. 3, 2013

(86) PCT No.: PCT/EP2013/061413
§ 371 (c)(1),
(2) Date: Dec. 4, 2014

(87) PCT Pub. No.: WO2013/182531
PCT Pub. Date: Dec. 12, 2013

(65) Prior Publication Data
US 2015/0167030 A1 Jun. 18, 2015

(30) Foreign Application Priority Data

Jun. 4, 2012 (EP) .................................... 12305629

(51) Int. Cl.
| | | |
|---|---|---|
| *C12N 9/18* | (2006.01) | |
| *C12P 7/56* | (2006.01) | |
| *C12N 9/24* | (2006.01) | |
| *C12N 15/00* | (2006.01) | |
| *C07H 21/04* | (2006.01) | |
| *C12N 9/42* | (2006.01) | |

(52) U.S. Cl.
CPC . *C12P 7/56* (2013.01); *C12N 9/18* (2013.01); *C12N 9/2437* (2013.01); *C12N 9/2445* (2013.01); *C07K 2319/02* (2013.01); *C07K 2319/20* (2013.01); *C07K 2319/70* (2013.01); *C12P 2203/00* (2013.01); *C12Y 301/01073* (2013.01)

(58) Field of Classification Search
CPC ........ C12N 9/2437; C12N 9/2445; C12P 7/10; C12P 7/56; C12Y 302/010191
USPC ................... 435/139, 200, 197, 252.3, 320.1
See application file for complete search history.

(56) References Cited

FOREIGN PATENT DOCUMENTS

| KR | 20110045975 | 5/2011 |
|---|---|---|
| WO | WO 2010/012805 | 2/2010 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Wieczorek, A. et al. "Engineering the cell surface display of cohesins for assembly of cellulosome-inspired enzyme complexes on *Lactococcus lactis*" Microbial Cell Factories, Sep. 2010, pp. 1-13, Vo. 9, No. 69.
Wieczorek, A. et al. "Effects of synthetic cohesin-containing scaffold protein architecture on binding dockerin-enzyme fusions on the surface of *Lactococcus lactis*" Microbial Cell Factories, 2012, pp. 1-13, vol. 160, No. 11.
Koukiekolo, R. et al. "Degradation of Corn Fiber by *Clostridium cellulovorans* Cellulases and Hemicellulases and Contribution of Scaffolding Protein CbpA" Applied and Environmental Microbiology, Jul. 1, 2005, pp. 3504-3511, vol. 71, No. 7.
Cha, J. et al. "Effect of Multiple Copies of Cohesins on Cellulase and Hemicellulase Activities of *Clostridium cellulovorans* Minicellulosomes" Journal of Microbiology and Biotechnology, 2007, pp. 1782-1788, vol. 17, No. 11.
Kataeva, I. et al. "Interaction between *Clostridium thermocellum* endoglucanase CelD and polypeptides derived from the cellulosome-integrating protein CipA: stoichiometry and cellulolytic activity of the complexes" Biochemical Journal, 1997, pp. 617-624, vol. 326, No. 2.
Wen, F. et al. "Yeast Surface Display of Trifunctional Minicellulosomes for Simultaneous Saccharification and Fermentation of Cellulose to Ethanol" Applied and Environmental Microbiology, Feb. 1, 2010, pp. 1251-1260, vol. 76, No. 4.
Hyeon, J. E. et al. "Production of minicellulosomes for the enhanced hydrolysis of cellulosic substrates by recombinant *Corynebacterium glutamicum*" Enzyme and Microbial Technology, 2011, pp. 371-377, vol. 48.
Sun, J. et al. "Direct Conversion of Xylan to Ethanol by Recombinant *Saccharomyces cerevisiae* Strains Displaying an Engineered Minihemicellulosome" Applied and Environmental Microbiology, Jun. 2012, pp. 3837-3845, vol. 78, No. 11.
Database EMBL [Online] Accession No. HC441374, "Sequence 9 from Patent WO2010012805" Feb. 20, 2010, pp. 1-3, XP-002697306.
Database Geneseq [Online] Accession No. AZM34659, "*Clostridium* sp. Cellulose-binding protein-A (CbpA) DNA SEQ: 6" Oct. 13, 2011, p. 1, XP-002697307.
Written Opinion in International Application No. PCT/EP2013/061413, Aug. 5, 2013, pp. 1-7.

* cited by examiner

*Primary Examiner* — Robert Mondesi
*Assistant Examiner* — Md. Younus Meah
(74) *Attorney, Agent, or Firm* — Saliwanchik, Lloyd & Eisenschenk

(57) ABSTRACT

The present invention relates to a polynucleotide encoding a recombinant scaffolding polypeptide comprising at least a signal peptide, a Cellulose Binding Domain, two cohesin domains and an S-layer Homology domain, wherein said isolated polynucleotide preferably comprises all or an active part of the nucleotide sequence as set forth in SEQ ID NO:2. The present invention further relates to vectors comprising such polynucleotides, recombinant lactic acid bacteria, and method for degrading a cellulosic biomass using such recombinant lactic acid bacteria.

10 Claims, 2 Drawing Sheets

SEQUENCE LISTING

<160> NUMBER OF SEQ ID NOS: 53

<210> SEQ ID NO 1
<211> LENGTH: 5547
<212> TYPE: DNA
<213> ORGANISM: Clostridium cellulovorans

<400> SEQUENCE: 1

```
atgcaaaaaa agaaatcgct gaatttattg ttagcattaa tgatggtatt tgctttagta      60
ctaccaagta taccagcttt agcagcgaca tcatcaatgt cagttgaatt ttacaactct     120
aacaaatcag cacaaacaaa ctcaattaca ccaataatca aaattactaa cacatctgac     180
agtgatttaa atttaaatga cgtaaaagtt agatattatt acacaagtga tggtacacaa     240
ggacaaactt tctggtgtga ccatgctggt gcattattag gaaatagcta tgttgataac     300
actagcaaag tgacagcaaa cttcgttaaa gaaacagcaa gcccaacatc aacctatgat     360
acatatgttg aatttggatt tgcaagcgga cgagctactc ttaaaaaagg acaatttata     420
actattcaag gaagaataac aaaatcagac tggtcaaact acactcaaac aaatgactat     480
tcatttgatg caagtagttc aacaccagtt gtaaatccaa agttacagg atatataggt     540 ggagctaaag tacttggtac agcaccaggt ccagatgtac catcttcaat aattaatcct     600
acttctgcaa catttgataa aaatgtaact aaacaagcag atgttaaaac tactatgact     660
ttaaatggta acacatttaa aacaattaca gatgcaaacg gtacagctct aaatgcaagc     720
actgattata gtgtttctgg aaatgatgta acaataagca aagcttattt agcaaaacaa     780
tcagtaggaa caactacatt aaactttaac tttagtgcag gaaatcctca aaaattagta     840
attacagtag ttgacacacc agttgaagct gtaacagcta caattggaaa agtacaagta     900
aatgctggag aaacggtagc agtaccagtt aacttaacaa agttccagc agctggttta     960 gcaacaattg aattaccatt aacttttgat tctgcatcat tagaagtagt atcaataact    1020
gctggagata tcgtattaaa tccatcagta aacttctctt ctacagtaag tggaagcaca    1080
ataaaattat tattcttaga tgatacatta ggaagccaat taatcactaa ggatggagtt    1140
tttgcaacaa taacatttaa agcaaaagct ataactggaa caactgcaaa agtaacttca    1200
gttaaattag ctggaacacc agtagttggt gatgcgcaat acaagaaaaa accttgtgca    1260
gttaacccag gaacagtaac tatcaatcca atcgataata gaatgcaaat tcagttgga    1320 acagcaacag taaaagctgg agaaatagca gcagtgccag taacattaac aagtgttcca    1380
tcaactggaa tagcaactgc tgaagcacaa gtaagttttg atgcaacatt attagaagta    1440
gcatcagtaa ctgctggaga tatcgtatta aatccaacag taaacttctc ttatacagta    1500
aacggaaatg taataaaatt attattccta gatgatacat taggaagcca attaattagt    1560
aaagatggag ttttttgtaac aataaactttc aaagcaaaag ctgtaacaag cacagtaaca    1620
acaccagtta cagtatcagg aacacctgta tttgcagatg gtacattagc agaagtacaa    1680
tctaaaacag cagcaggtag cgttacaata aatattggag atcctatact agaaccaaca    1740
ataagccctg taactgcaac ttttgataaa aaagcaccag cagacgttgc aacaacaatg    1800
acattaaatg gttatacatt taacggaatc acaggattaa caacatcaga ctacagtatt    1860
tcaggtaatg tagtgaaaat tagccaagca tatttagcta acaaccagt tggagatctt    1920 acattaacat ttaacttctc aaatggtaat aaaactgcaa cagctaaatt agtagtatca    1980
atcaaagatg caccaaaaac tgtaacagct acagttggaa cagcaacagt aaacgctgga    2040
gaaacagtag cagtaccagt aacattatca aatgtttcag gaatatcaac tgctgaatta    2100
```

```
caattaagtt tgatgcaac attattagaa gtagtatcaa taactgctgg agatatcgta   2160
ttaaacccat cagtaaactt ctcttctgta gtaaacggaa gcacaataaa attattattc   2220
ctagatgata cattaggaag ccaattaatc agtaaagatg gagttttcgc aacaataaac   2280
ttcaaagcaa aatcggtaac aagcacagta acaacaccag ttaaagtatc aggaacacct   2340
gtatttgcag atggtacatt agctgagtta agctatgaaa cagtagcagg tagcgttaca   2400
ataaatgcaa ttggacctgt taaaactgta acagctacag ttggaacagc aacagtaaaa   2460
tcaggagaaa cagtagcagt accagtaaca ttatcaaatg ttccaggaat agcaactgct   2520
gaattacaat taagttttga tgcaacatta ttagaagtag catcaataac tgttggagat   2580
atcgtattaa acccatcagt aaacttctct tctgtagtaa acggaagcac aataaaatta   2640
ttattcctag atgatacatt aggaagccaa ttaatcagca aagatggagt tttagcaaca   2700
ataaacttca agcaaaaac tgtaacaagc acagtaacaa caccagtagc agtatcagga   2760
acacctgtat ttgcagatgg tacattagca gaattacaat ctaaaacagt agcaggtagc   2820
gttacaatag aaccaagtca acctgttaaa actgtaacag ctacagttgg aacagcaaca   2880
gtaaaatcag gagaaacagt agcagtacca gtaacattat caaatgttcc aggaatagca   2940
actgctgaat tacaagtagg cttttgatgca acattattag aagtagcatc aataactgtt   3000
ggagatatcg tattaaaccc atcagtaaac ttctcttctg tagtaaacgg aagcacaata   3060
aaattattat tcctagatga tacattagga agccaattaa tcagtaaaga tggagtttta   3120
gcaacaataa acttcaaagc aaaaactgta acaagcaaag taacaacacc agtagcagta   3180
tcaggaacac ctgtatttgc agatggtaca ttagcagaat aaatatgaa acagtagca   3240 ggtagcgtta caatagaacc aagtcaacct gttaaaactg taacagctac agttggaaca   3300
gcaacagtaa aatcaggaga aacagtagca gtaccagtaa cattatcaaa tgttccagga   3360
atagcaactg ctgaattaca gtaggctttt gatgcaacat tattagaagt agcatcaata   3420
actgttggag atatcgtatt aaacccatca gtaaacttct cttctgtagt aaacggaagc   3480
acaataaaat tattattcct agatgataca ttaggaagcc aattaatcag caaagatgga   3540
gttttagcaa caataaactt caaagcaaaa actgtaacag caaagtaac aacaccagta   3600 gcagtatcag gaacacctgt atttgcagat ggtacattag cagaattaaa atatgaaaca   3660
gtagcaggta gcgttacaat agaaccaagt caacctgtta aaactgtaac agctacagtt   3720
ggcacagcaa caggtaaagt tggggaaaca gtagcggtac cagtaacatt atcaaatgtt   3780
ccaggaatag caactgctga agtacaagta ggttttgatg caacattatt agaagtagca   3840
tcaataactg ctggagatat cgtattaaat ccatcagtaa acttctcttc tgtagtaaat   3900
ggaagcacaa taaaaatatt attcctagat gatacattag gaagccaatt aatcagtaaa   3960
gatggagttt tcgcaacaat aaacttcaaa ataaaagctg taccaagcac aggaacaaca   4020
ccagtagcaa tatcaggaac acctgtatttt gcagatggta cattagcaga agtacaatat   4080
aaaacagtag caggtagtgt tacaatagct gctgcagata tcaaagctgt aaaagctaca   4140
gttggaacag caacaggtaa agctggggat acagtagcag taccagtaac attatcaaat   4200
gtttcaggaa tagcaacagt tgaactacaa ttaagctttg atgcaacatt attagaagta   4260
gcatcaataa ctgctggaga tatcgtatta aatccatcag taaacttctc ttctgtagta   4320
aatggaagca ataaaaat attattccta gatgatacat taggaagcca attaatcagt   4380
aaagatggag ttttcgcaac agtaaacttc aaagttaaat caactgcaac aaatagtgca   4440
```

```
gtaacaccag ttacagtatc aggaacacct gtatttgcag atggtacatt agcagagtta      4500
aaatctgaat cagcagctgg aaggctaact atattaccaa ctgtaataat agttgactca      4560
acagtagctc caacagctgt aacatttgat aaagctaatc aagcagatgc tgcaataaca      4620
atgacattaa acggaaacac attctcagca ataaagaatg aacagctac attagtaaaa       4680 ggaactgatt acacagtttc agaaaatgta gtaacaatca gcaaagctta cttagctaag      4740
caaactggaa cagttacatt agaatttgta tttgacaaag gaaattcagc taaagttgtt      4800
gtagctgtaa aagaaattca aattgtaaat tcaacaataa ctccagtagt agcaacattt      4860
gaaaaaactg ctgctaaaca agcagatgtt gtagtaacaa tgtctttaaa tggtaacaca      4920
ttctcagcaa taagaatgg aacaactaca ttagtaaaag gaactgatta cacaatttca       4980
ggaagcacag taacaatcag caaagcttac ctagctacat agcgagtgg aagtgcaaca       5040 ttagaatttg tatttaacca aggggctagt gcaaaattac gattaactat agtaccagca      5100
gtagtagatc cagtagtaac tgattttgct gttaaaattg acaagtatc tgcagcagca       5160 ggttctacag ttaaagttcc agtatcatta attaatgttt ctaaggttgg aaatgttttgt    5220 gtagctgaat acaaaatcag ctttgactca agtgtactta catatgtagg aactacagca      5280
ggaacatcaa tcaaaaatcc tgcagttaac ttctcatcac aacttaacgg aaacactatt      5340
acattattat tctttgacaa tacaattgga atgaattaa taacagctga tggtcaattc       5400
gctacaatcg aattcaaagt taatgcagca gctacttcag gaacaactgc agaagttaaa      5460
gtagcaacta aagctcatt cgctgatgca tcattaactg aaatcactaa agtagctaca      5520
gttaacggaa gtgttaaagt tagctaa                                          5547

<210> SEQ ID NO 2
<211> LENGTH: 1737
<212> TYPE: DNA
<213> ORGANISM: artificial sequence
<220> FEATURE:
<223> OTHER INFORMATION: mini-CbpA

<400> SEQUENCE: 2
atgcaaaaaa agaaatcgct gaatttattg ttagcattaa tgatggtatt tgctttagta       60
ctaccaagta taccagcttt agcagcgaca tcatcaatgt cagttgaatt ttacaactct      120
aacaaatcag cacaaacaaa ctcaattaca ccaataatca aaattactaa cacatctgac      180
agtgatttaa atttaaatga cgtaaaagtt agatattatt acacaagtga tggtacacaa      240
ggacaaactt tctggtgtga ccatgctggt gcattattag gaatagcta tgttgataac       300 actagcaaag tgacagcaaa cttcgttaaa gaaacagcaa gcccaacatc aacctatgat      360
acatatgttg aatttggatt tgcaagcgga gcagctactc ttaaaaaagg acaatttata      420
actattcaag gaagaataac aaaatcagac tggtcaaact acactcaaac aaatgactat      480
tcatttgatg caagtagttc aacaccagtt gtaaatccaa agttacagg atatataggt       540 ggagctaaag tacttggtac agcaccaggt ccagatgtac catcttcaat aattaatcct      600
acttctgcaa catttgataa aaatgtaact aaacaagcag atgttaaaac tactatgact      660
ttaaatggta acacatttaa aacaattaca gatgcaaacg gtacagctct aaatgcaagc      720
actgattata gtgtttctgg aaatgatgta acaataagca aagcttattt agcaaaacaa      780
tcagtaggaa caactacatt aaactttaac tttagtgcag gaaatcctca aaaattagta      840
attacagtag ttgacacacc agttgaagct gtaacagcta caattggaaa agtacaagta      900
aatgctggag aaacggtagc agtaccagtt aacttaacaa aagttccagc agctggttta      960
```

```
gcaacaattg aattaccatt aactttttgat tctgcatcat tagaagtagt atcaataact    1020
gctggagata tcgtattaaa tccatcagta aacttctctt ctacagtaag tggaagcaca    1080
ataaaattat tattcttaga tgatacatta ggaagccaat taatcactaa ggatggagtt    1140
tttgcaacaa taacatttaa agcaaaagct ataactggaa caactgcaaa agtaacttca    1200
gttaaattag ctggaacacc agtagttggt gatgcgcaat tacaagaaaa accttgtgca    1260
gttaacccag gaacagtaac tatcaatcca atcgataata gaatgcaaat ttcgttggaa    1320
acagcaacag taaaagctgg agaaatagca gcagtgccag taacattaac aagtgttcca    1380
tcaactggaa tagcaactgc tgaagcacaa gtaagttttg atgcaacatt attagaagta    1440
gcatcagtaa ctgctggaga tatcgtatta aatccaacag taaacttctc ttatacagta    1500
aacggaaatg taataaaatt attattccta gatgatacat taggaagcca attaattagt    1560
aaagatggag ttttttgtaac aataaacttc aaagcaaaag ctgtaacaag cacagtaaca    1620
acaccagtta cagtatcagg aacacctgta tttgcagatg gtacattagc agaagtacaa    1680
tctaaaacag cagcaggtag cgttacaata aatattggag atcctatact agaataa       1737

<210> SEQ ID NO 3
<211> LENGTH: 414
<212> TYPE: DNA
<213> ORGANISM: artificial sequence
<220> FEATURE:
<223> OTHER INFORMATION: Cohesin 1

<400> SEQUENCE: 3
gtaacagcta caattggaaa agtacaagta aatgctggag aaacggtagc agtaccagtt      60
aacttaacaa agttccagc agctggttta gcaacaattg aattaccatt aactttttgat    120 tctgcatcat tagaagtagt atcaataact gctggagata tcgtattaaa tccatcagta    180
aacttctctt ctacagtaag tggaagcaca ataaaattat tattcttaga tgatacatta    240
ggaagccaat taatcactaa ggatggagtt tttgcaacaa taacatttaa agcaaaagct    300
ataactggaa caactgcaaa agtaacttca gttaaattag ctggaacacc agtagttggt    360
gatgcgcaat tacaagaaaa accttgtgca gttaacccag gaacagtaac tatc          414

<210> SEQ ID NO 4
<211> LENGTH: 408
<212> TYPE: DNA
<213> ORGANISM: artificial sequence
<220> FEATURE:
<223> OTHER INFORMATION: Cohesin 2

<400> SEQUENCE: 4
atgcaaattt cagttggaac agcaacagta aaagctggag aaatagcagc agtgccagta     60
acattaacaa gtgttccatc aactggaata gcaactgctg aagcacaagt aagttttgat    120
gcaacattat tagaagtagc atcagtaact gctggagata tcgtattaaa tccaacagta    180
aacttctctt atacagtaaa cggaaatgta ataaaattat tattcctaga tgatacatta    240
ggaagccaat taattagtaa agatggagtt tttgtaacaa taaacttcaa agcaaaagct    300
gtaacaagca cagtaacaac accagttaca gtatcaggaa cacctgtatt tgcagatggt    360
acattagcag aagtacaatc taaaacagca gcaggtagcg ttacaata               408

<210> SEQ ID NO 5
<211> LENGTH: 402
<212> TYPE: DNA
```

<213> ORGANISM: artificial sequence
<220> FEATURE:
<223> OTHER INFORMATION: Cohesin 3

<400> SEQUENCE: 5

| | | | | | |
|---|---|---|---|---|---|
| gtaacagcta | cagttggaac | agcaacagta | aacgctggag | aaacagtagc agtaccagta | 60 |
| acattatcaa | atgtttcagg | aatatcaact | gctgaattac | aattaagttt tgatgcaaca | 120 |
| ttattagaag | tagtatcaat | aactgctgga | gatatcgtat | aaacccatc agtaaacttc | 180 |
| tcttctgtag | taaacggaag | cacaataaaa | ttattattcc | tagatgatac attaggaagc | 240 |
| caattaatca | gtaaagatgg | agtttttcgca | acaataaact | tcaaagcaaa atcggtaaca | 300 |
| agcacagtaa | caacaccagt | taaagtatca | ggaacacctg | tatttgcaga tggtacatta | 360 |
| gctgagttaa | gctatgaaac | agtagcaggt | agcgttacaa | ta | 402 |

<210> SEQ ID NO 6
<211> LENGTH: 402
<212> TYPE: DNA
<213> ORGANISM: artificial sequence
<220> FEATURE:
<223> OTHER INFORMATION: Cohesin 4

<400> SEQUENCE: 6

| | | | | | |
|---|---|---|---|---|---|
| gtaacagcta | cagttggaac | agcaacagta | aaatcaggag | aaacagtagc agtaccagta | 60 |
| acattatcaa | atgttccagg | aatagcaact | gctgaattac | aattaagttt tgatgcaaca | 120 |
| ttattagaag | tagcatcaat | aactgttgga | gatatcgtat | aaacccatc agtaaacttc | 180 |
| tcttctgtag | taaacggaag | cacaataaaa | ttattattcc | tagatgatac attaggaagc | 240 |
| caattaatca | gcaaagatgg | agttttagca | acaataaact | tcaaagcaaa aactgtaaca | 300 |
| agcacagtaa | caacaccagt | agcagtatca | ggaacacctg | tatttgcaga tggtacatta | 360 |
| gcagaattac | aatctaaaac | agtagcaggt | agcgttacaa | ta | 402 |

<210> SEQ ID NO 7
<211> LENGTH: 402
<212> TYPE: DNA
<213> ORGANISM: artificial sequence
<220> FEATURE:
<223> OTHER INFORMATION: Cohesin 5

<400> SEQUENCE: 7

| | | | | | |
|---|---|---|---|---|---|
| gtaacagcta | cagttggaac | agcaacagta | aaatcaggag | aaacagtagc agtaccagta | 60 |
| acattatcaa | atgttccagg | aatagcaact | gctgaattac | aagtaggctt tgatgcaaca | 120 |
| ttattagaag | tagcatcaat | aactgttgga | gatatcgtat | aaacccatc agtaaacttc | 180 |
| tcttctgtag | taaacggaag | cacaataaaa | ttattattcc | tagatgatac attaggaagc | 240 |
| caattaatca | gtaaagatgg | agttttagca | acaataaact | tcaaagcaaa aactgtaaca | 300 |
| agcaaagtaa | caacaccagt | agcagtatca | ggaacacctg | tatttgcaga tggtacatta | 360 |
| gcagaattaa | atatgaaaac | agtagcaggt | agcgttacaa | ta | 402 |

<210> SEQ ID NO 8
<211> LENGTH: 402
<212> TYPE: DNA
<213> ORGANISM: artificial sequence
<220> FEATURE:
<223> OTHER INFORMATION: Cohesin 6

<400> SEQUENCE: 8

| | | | | | |
|---|---|---|---|---|---|
| gtaacagcta | cagttggaac | agcaacagta | aaatcaggag | aaacagtagc agtaccagta | 60 |

| | |
|---|---|
| acattatcaa atgttccagg aatagcaact gctgaattac aagtaggctt tgatgcaaca | 120 |
| ttattagaag tagcatcaat aactgttgga gatatcgtat taaacccatc agtaaacttc | 180 |
| tcttctgtag taaacggaag cacaataaaa ttattattcc tagatgatac attaggaagc | 240 |
| caattaatca gcaaagatgg agttttagca acaataaact tcaaagcaaa aactgtaaca | 300 |
| agcaaagtaa caacaccagt agcagtatca ggaacacctg tatttgcaga tggtacatta | 360 |
| gcagaattaa aatatgaaac agtagcaggt agcgttacaa ta | 402 |

```
<210> SEQ ID NO 9
<211> LENGTH: 402
<212> TYPE: DNA
<213> ORGANISM: artificial sequence
<220> FEATURE:
<223> OTHER INFORMATION: Cohesin 7

<400> SEQUENCE: 9
```

| | |
|---|---|
| gtaacagcta cagttggcac agcaacaggt aaagttgggg aaacagtagc ggtaccagta | 60 |
| acattatcaa atgttccagg aatagcaact gctgaagtac aagtaggttt tgatgcaaca | 120 |
| ttattagaag tagcatcaat aactgctgga gatatcgtat taaatccatc agtaaacttc | 180 |
| tcttctgtag taaatggaag cacaataaaa atattattcc tagatgatac attaggaagc | 240 |
| caattaatca gtaaagatgg agttttcgca acaataaact tcaaaataaa agctgtacca | 300 |
| agcacaggaa caacaccagt agcaatatca ggaacacctg tatttgcaga tggtacatta | 360 |
| gcagaagtac aatataaaac agtagcaggt agtgttacaa ta | 402 |

```
<210> SEQ ID NO 10
<211> LENGTH: 405
<212> TYPE: DNA
<213> ORGANISM: artificial sequence
<220> FEATURE:
<223> OTHER INFORMATION: Cohesin 8

<400> SEQUENCE: 10
```

| | |
|---|---|
| gtaaaagcta cagttggaac agcaacaggt aaagctgggg atacagtagc agtaccagta | 60 |
| acattatcaa atgtttcagg aatagcaaca gttgaactac aattaagctt tgatgcaaca | 120 |
| ttattagaag tagcatcaat aactgctgga gatatcgtat taaatccatc agtaaacttc | 180 |
| tcttctgtag taaatggaag cacaataaaa atattattcc tagatgatac attaggaagc | 240 |
| caattaatca gtaaagatgg agttttcgca acagtaaact tcaaagttaa atcaactgca | 300 |
| acaaatagtg cagtaacacc agttacagta tcaggaacac ctgtatttgc agatggtaca | 360 |
| ttagcagagt aaaatctga atcagcagct ggaaggctaa ctata | 405 |

```
<210> SEQ ID NO 11
<211> LENGTH: 420
<212> TYPE: DNA
<213> ORGANISM: artificial sequence
<220> FEATURE:
<223> OTHER INFORMATION: Cohesin 9

<400> SEQUENCE: 11
```

| | |
|---|---|
| tttgctgtta aaattgacaa agtatctgca gcagcaggtt ctacagttaa agttccagta | 60 |
| tcattaatta atgtttctaa ggttggaaat gtttgtgtag ctgaatacaa aatcagctt | 120 |
| gactcaagtg tacttacata tgtaggaact acagcaggaa catcaatcaa aaatcctgca | 180 |
| gttaacttct catcacaact taacggaaac actattacat tattattctt tgacaataca | 240 |

```
attggaaatg aattaataac agctgatggt caattcgcta caatcgaatt caaagttaat    300
gcagcagcta cttcaggaac aactgcagaa gttaaagtag caactataag ctcattcgct    360
gatgcatcat taactgaaat cactaaagta gctacagtta acggaagtgt taaagttagc    420
```

<210> SEQ ID NO 12
<211> LENGTH: 234
<212> TYPE: DNA
<213> ORGANISM: artificial sequence
<220> FEATURE:
<223> OTHER INFORMATION: SLH 1

<400> SEQUENCE: 12

```
ataattaatc ctacttctgc aacatttgat aaaaatgtaa ctaaacaagc agatgttaaa     60
actactatga ctttaaatgg taacacattt aaaacaatta cagatgcaaa cggtacagct    120
ctaaatgcaa gcactgatta tagtgtttct ggaaatgatg taacaataag caaagcttat    180
ttagcaaaac aatcagtagg aacaactaca ttaaacttta actttagtgc agga          234
```

<210> SEQ ID NO 13
<211> LENGTH: 210
<212> TYPE: DNA
<213> ORGANISM: artificial sequence
<220> FEATURE:
<223> OTHER INFORMATION: SLH 2

<400> SEQUENCE: 13

```
acaataagcc ctgtaactgc aacttttgat aaaaaagcac cagcagacgt tgcaacaaca     60
atgacattaa atggttatac atttaacgga atcacaggat taacaacatc agactacagt    120
atttcaggta atgtagtgaa aattagccaa gcatatttag ctaaacaacc agttggagat    180
cttacattaa catttaactt ctcaaatggt                                     210
```

<210> SEQ ID NO 14
<211> LENGTH: 222
<212> TYPE: DNA
<213> ORGANISM: artificial sequence
<220> FEATURE:
<223> OTHER INFORMATION: SLH 3

<400> SEQUENCE: 14

```
acagtagctc caacagctgt aacatttgat aaagctaatc aagcagatgc tgcaataaca     60
atgacattaa acggaaacac attctcagca ataaagaatg gaacagctac attagtaaaa    120
ggaactgatt acacagtttc agaaaatgta gtaacaatca gcaaagctta cttagctaag    180
caaactggaa cagttacatt agaatttgta tttgacaaag ga                       222
```

<210> SEQ ID NO 15
<211> LENGTH: 231
<212> TYPE: DNA
<213> ORGANISM: artificial sequence
<220> FEATURE:
<223> OTHER INFORMATION: SLH 4

<400> SEQUENCE: 15

```
acaataactc cagtagtagc aacatttgaa aaaactgctg ctaaacaagc agatgttgta     60
gtaacaatgt ctttaaatgg taacacattc tcagcaataa agaatggaac aactacatta    120
gtaaaaggaa ctgattacac aatttcagga agcacagtaa caatcagcaa agcttaccta    180
gctacattag cagatggaag tgcaacatta gaatttgtat ttaaccaagg g             231
```

<210> SEQ ID NO 16
<211> LENGTH: 3204
<212> TYPE: DNA
<213> ORGANISM: Clostridium cellulovorans

<400> SEQUENCE: 16

```
atgaagaaga gaaacagaat actatcattt ttgctagttt tagcaatggt attctcttgt      60
gttgttagca aaccgttggt aaaagtatct gccgcagaag ctaactacac aacaaaaggc     120
actacgacac agatatatct tagtgccttt gcacaaaata ctgatgactg ggcttggatg     180
agtatgggag atactgctag cttagtatat caagacgtaa caaatttcaa tgccatcgac     240
gctactagtg cctttgcaaa ggcaaatggt actgcaaact tgggttaca ggttgttgat      300
ggaaatcttg ctgcaggaga aaaagtaca ttaaaattcc atattggaac agttactatt      360
aaagcaactg gatataatga tgttgtggtt aatcttaaca aggattattc agaagcatat     420
gcagcagaaa agtttcttg gggaatcaca ggaaacaata catcaatttt actaaatgat      480
tatttaccaa cagatgcagc agcgaaagca acgtatctac aaaagattac tagtgtaaaa     540
gcagatgtta cattatcaga atatcaattt gttaaaccag catcaactgg gtcaacttct     600
gaaagtgtat actcatcagg tgatgcaaca aagatttatg ctagtgcgtt tgcacaaaat     660
actgatgact gggcttggat gagcatggga gatactgctg tttttaacata tcaaactgct     720
acaaacgtaa atgctatcaa tgcaggtact gcatttgcaa gtgcaaatgg aactgcaaac     780
tttggtatcc aaattgttga cggaaaccta gctgctgcag gagactcaag tacattaaaa     840
ttccatgttg gaacagttac aattaaagca acaggttatg atgatcttgt agttgctcta     900
aataaagatt attcagaagc atatactgca gaaaaaatga cttggggact tactggaaat     960
aacacacaaa tttttattaaa tagttattta ccaacgatg caactgcaaa agctgcatat    1020
ctacaaaaaa taacttctgt tacagctgat gttacagtaa cagattatca atcgattaaa    1080
ccagcaacag caactgggga agttctttac acaacaccag gtgttgaaac aaagatttct    1140
gctagtgctt ttgcacaaaa caccgatgac tgggcttgga tgagcgtagg tgatggtgtt    1200
agtcttcaat atcaaactga tacaacttta aatgctatta gtgctgctgg tacattagca    1260
aaagcaaatg ctacagcaaa cttggtata aatattgttg atggaaatct tgctgctgga    1320
gatgcaaaca cattaaagtt ccatgttgga acagttacaa ttaaagcaac aggttatgat    1380
gaccttgtga ttaacttaaa taagattac tcagaagcat ttgcagcaga aaagcttct    1440
tggggactta caggaaacac aaaacaaatt ttattaaact cttatttacc aacagatgca    1500
acagcaaaag taaactatct tcaaaaggtt actagtgtta cagctgatgt aaaagtaaca    1560
gattatacgt ttattaaata tgtaccacca gcaccagaat tccctgctga ttacactcac    1620
ccaacagaaa tgagaggtct ttctgctatg gatttagtaa aagacatgaa gattggttgg    1680
aacttaggaa atactttaga atcagttggc ggagaaactg gttggggtaa tcctgtaaca    1740
acaaagaaaa tgtttgatac attaaaggca gctggcttta tacagttcg tattccagta    1800
agatgggatg aaaactatat tgatgctaat tatactattg atccagcata tatggctcgt    1860
gttgaaacag ttgtaaacta tgcacttgct aacgatatgt atgccattgt taatattcac    1920
cataataaat tccaaggtca atttgatgaa gcacacaaag ctgccatcat taacgaaggt    1980
actattgtat ggactcaaat tgcaaaccac tttaaagatt atagtgataa attaatattt    2040
gatacaataa atgaaccaag acatgaagaa gactggggttg gtacttcaga atactttaat    2100
gtcttaaatg aatataacgc aaaaatagtt cctgtaatac gtgcaactgg cgaaaataat    2160
```

```
gctaagagac ttataatggt tcctacttat tgtgcttctt cagattatcc taaggttgct    2220
ggtatggtag taccaaatga tcctaatgtt gcagtatcta tccacgctta cataccatat    2280
aatttagcac ttaatatagc tccaggtaca ccaactacct ttggtgatgc tgacgcagca    2340
tttattgaca agactttcag aatgttaaac aacacatttg ttaaaaaggg aattcctgtt    2400
attatcggtg aattcgcgat tacagataaa gataacttac aagacagaat taactttacg    2460
aagttctatg tatcaacagc tactgcttat ggaatgccat gtttgtggtg ggataataat    2520
aattttggta gcacaggtga gagactgggg cttttaaata gaaaaaccct tacattccct    2580
tatcctgaat tagtacaagc tatgaaagat ggtttcaaca atccaagaga tctttcaacc    2640
gttgatccaa acgtattatt tagtggtaca gcatcttgta caggctggag cacagcactt    2700
tcattatcct atggcttaga ttttgtagat actgaattta caaatgattt tacaatagct    2760
gtagattaca caagtgaaaa tgtacctcaa ttagtcctat atggaaactt gactggtaca    2820
ggttgggtta tggtaaaacc ttcaacaatc aaaacaagcg caactacaaa gactgcatac    2880
tttactataa atgatatggt aagtgcatat aagaaagctc ttgcaaacta tgatagctat    2940
ggtaaggtat taccaggaat ccaaggtatt ttagttggag atactggtgc agaccttaca    3000
gtaacaaaag tttacaagaa tgcacaacct gtaaatcttc taggcgatgt agacggtaat    3060
gatgtagtta attcacttga tttttgagtta ttaaagaagt atgtattaaa caatgataca    3120
atgataaaca aagctagtgc agatttaaat aaggatggaa aaatcaacat aattgatctt    3180
gcattcttaa aaaaagcaat ataa                                           3204

<210> SEQ ID NO 17
<211> LENGTH: 2148
<212> TYPE: DNA
<213> ORGANISM: Clostridium cellulovorans

<400> SEQUENCE: 17
gtgtttaaca tatctaagaa aaaagcgcaa gctcttcttt tatcaggaat cttgggtgca      60 acttcatttta caccagctgt attggtaaaa ggtgaaacaa cagcgactcc aacattcaat    120
tatggagaag cattacaaaa gtcaataatg ttttatgaat tccaacgttc tggaaagtta    180
ccaacggata ttcgtagtaa ttggcgtggt gattctggaa caaaagatgg ctctgatgta    240
ggagttgatt taactggtgg atggtatgat gctggagacc acgttaaatt taatctgcca    300
atgtcttata ctgtggcaat gcttgcatgg tcattaagtg aagacaaagc agcttacgaa    360
aaaagcggcc aattagatta ccttgttaag gaaataaaat gggctacaga ttatctaatg    420
aagtgccata cggcaccaaa tgaatactat tatcaagttg gtgatggtgg agctgatcac    480
aaatggtggg gacctgcaga agtaatgcag atggcaagac cggcttataa agtagatttg    540
caaaaaccag gatcatcagt tgtcgctgaa acagcagcag cattagcttc tacagctttt    600
gcattaaaag acatagataa agcgtattca gaacaatgta ttcagcatgc aaaagaactt    660
tataactttg ctgatacaac aaagagtgat gctggttata cagcagcaaa tacatattac    720
aattcatgga gtggatacta tgatgaatta tcatgggctg cagcatggct ttacatggca    780
acaaatgatg catcatatct agaaaaagcg gaatcatatg ttccattttg gaaggttgaa    840
cagcaaacaa ccactatagc atatagatgg gcgcattgtt gggatgatgt acatttcgga    900
gctcaattac tccttgccag attaacagga aaatcaatat acaagaatc agttgaaaga    960 aaccttgatt attggacaac tggttatgat ggaaatataaaa taagtacac tccaaaaggt   1020 ttagcttgga tggattcttg gggctcatta agatatgcaa ctacaacggc attccttgcc   1080
```

```
gatgtttatg caagctcaga tgtttgttct atttctaagg tagatacata taagaatttt    1140
gctaagagtc aagctgatta tgctttagga agtactggaa gaagttttgt ggtaggattt    1200
ggtgaaaatg ctccaaagaa accacatcat agaactgccc atagttcatg gtcagatcaa    1260
caagtaaatc caacagacca tagacatgtt ttatatggtg cttagttgg aggaccagat     1320 gccagtgatg gttatactga tgctattgac aatttacta ataatgaggt ggcttgtgat     1380
tataatgcag gatttgtagg acttttagct agacaatatt ctaaatatgg cggagatcca    1440
atacctgatt ttaaagcgat agaaaagcca accaacgatg agttctttgt cgaagcagga    1500
gtaaattgta caggtccaaa ttttgtagaa attaaagctt tagttaataa tagaacagga    1560
tggccagcaa gaatgggaga taaactttca ttcaaatact tcataaatgt aagtgaattt    1620
gttaatgctg gttacagtgc agatgattta aaggttactg ttggttacaa tactggcgga    1680
actgtatcaa acctaatccc atgggataag gaaaataata tttattatgt aaatgttgat    1740
ttcacagggg taaagattta tccaggtgga caatcagatt ataaaaaaga aattcaattt    1800
agaatttcag gaattcaaaa tgttaatatt tgggataatt ctgatgactt ctcttatgag    1860
gggattacaa aaactccagg tgaaacacct gtgaaggtta caaacatccc agtttatgat    1920
aatggagtta aggtattcgg aaatgaacca ggaactacta agccacctgt tatagctggt    1980
gatgtaaaca ataatggtat cgtgaattca atggatttag cgatgttaaa gaaatatata    2040
cttggatacg aagtagaaat gaataaagag gcttcagatt taaataaaga tggtaagatt    2100
aatgccattg atttcgctct tttaaagaaa ctactttat cacagtag                  2148
```

<210> SEQ ID NO 18
<211> LENGTH: 2151
<212> TYPE: DNA
<213> ORGANISM: Clostridium cellulovorans

<400> SEQUENCE: 18

```
atgaaaaaat taggttctat cttagctagc gtggttatgt tagcttctat cacagcacca     60
ttaaaggcac cagtaaaagt gtcagctaca gaaaattaca actacgggga agcattacaa    120
aagggaatta tgttctatga atttcaaaga tcaggagact tacctgaaaa cggtagaaat    180
aactggcgtg gagattctgg attgactgat ggtaaagaca atggtctaga tcttactgga    240
ggttggtatg atgctggaga tcacgtaaaa ttcaatttgc caatggctta cactgtttca    300
atgttatcat ggagtgttta tgaaagtcgt ggtgcatatg aaaaaagtgg tcaacttcct    360
tacatattag acaatataaa atgggctaca gattacttga taaaatgcca tccaagtcca    420
aatgaatact actatcaagt tggtgatgct gcagcggatc attcatggtg gggatctgcg    480
gaagttatgc caatggcaag accatcattt aaagttgata cagctaatcc cggatcagct    540
gtcgtaggac aaactgccgc tgcgttagca gcagcttcaa taattttcaa ggatacagat    600
ccttcttatt ctgagctttg cttaaagcac gcaaagaat tattcacttt tgcagatact    660
acaagaagtg atgctggata taaggcagct cagggatgtt atagttcatg gagtggtttt    720
tatgatgaat taacttgggc ggctacatgg ctgaatatgg caactggcga ctcagcttat    780
cttgataagg cagagtctta tgtgccaaac tggggagtag agcttggaac aagcacgcct    840
aaatatactt gggcgcataa ttgggataac tgtatctttg gttcttactt actacttgct    900
aggttgacaa ataaaccact ttataaagaa tgcgcagaaa gaaatttaga ttggtggtca    960
acaggcgttg gtacacaaag agtaccatat agcgcaaaag ggctagcagt tttagatatg   1020
```

-continued

```
tggggatctc ttagatacgc aacaactcaa gctttccttg caagtgttta tgctgattgg    1080
tctggttgtg atgttacaaa ggcaactgct tatgaaaatt ttgcaaagag tcaaattgat    1140
tatgctcttg gaagcactgg aagaagtttt gtagtaggct ttggggaaaa ttctccaaca    1200
catcctcatc atagaactgc acacagtact tggatgggat atttaacatg taatattcct    1260
gattacagta ggcatacgct ttatggagca ttagttggag gtccagatac tagcgataag    1320
tacactgatg acataaataa ctatcaaaat aatgaggttg cttgtgatta taatgcaggc    1380
tttgttggga tccttgctaa aatgtacgac aaatacggtg gtacaccaat tgaaaatttc    1440
aaagctattg aaacgccagt tgatgaatac ctagcttatg gtagttcaag tggaactagt    1500
ggaaatgaac ttcaattaat ggtttctatt cgtaatcaaa ctggttggcc agcaagaggt    1560
agtgataaac tatctgctag atactttatg gatattacag aagaaattaa agctggtata    1620
aaaccaagtg actttacagc aaaggctagt acctcaggag ttaaactttc tgggcttata    1680
ccttgggatg ttgataaaaa catatactat ataaatattg attttacagg aactaatatc    1740
tctcctataa acaacaacac ttacaaaaaa gatgtttata tgtcgatagg tattccttat    1800
ggaacagcga taaactgtgc aaatgatttc tcattccaag ggcttacagc tactactggt    1860
ggacaagatg gagttaaaac aaaatatatt cctatctacg ataatggagt aaaggttgct    1920
ggtgaagaac ctactctaat agttaacccct actataaaaa agggtgatgt taataatgat    1980
acaaagatat ctgccatgga tcttgcacta ctgaagaaac atattatggg tacctcaacc    2040
ttaacaggag atgcatttac agcagcagat gtagattcaa atgggaaagt aaattcaata    2100
gatttagctt tattgaaaaa atacatttta ggtcaaataa ctagtttcta g              2151
```

<210> SEQ ID NO 19
<211> LENGTH: 2184
<212> TYPE: DNA
<213> ORGANISM: Clostridium cellulovorans
<400> SEQUENCE: 19

```
atgagaaaaa gattaaataa gatcgttgct gttgctttaa ctgcaacaac tatatcatca     60
gtagcagcta ctgttaatac agctcaagtt tcagctgcac cagtagtgcc aaataatgag    120
tatgttcaac actttaagga tatgtacgct aagatccata tgcaaacaa tggatacttc     180 agtgatgaag gaataccctta tcacgcagtt gaaacattaa tggttgaagc accagactat    240
ggtcatgaaa ctacaagtga agctttcagt tactatatgt ggcttgaagc tatgaacgct    300
aagcttactg gagatttctc aggattcaaa aaagctgggg atgtaactga aaagtacata    360
attccaggtg agactgatca accaagcgca agtatgagca attatgatcc aaataagcca    420
gctacatatg cagctgaaca tccagatcca agcatgtacc catctcaatt acaatttggt    480
gctgctgtag gtaaggatcc attatacaat gaattaaaat ctacttatgg aactagccaa    540
gtatatggta tgcattggtt actagatgtt gataactggt atggttttgg tggtgcaaca    600
agcacaagcc agtatacat caacactttc caaagaggtg ttcaagaatc ttgttgggaa    660
actgtgccac aaccatgtaa agacgaaatg aagtacggtg gaagaaacgg tttcttagat    720
ctattcactg gtgattcaca atacgcaact caatttaaat atactaacgc tccagacgca    780
gatgctcgtg cagttcaagc tacttactat gcacaattag ctgctaaaga tgggggagta    840
gacatcagct catatgtagc aaaatctact aagatgggtg acttcttaag atattcattc    900
tttgataaat actttagaaa agttggaaat tcaacacaag caggaactgg atatgattca    960
gctcaatacc tattaaactg gtactatgct tggggtggtg aatcagctc aaactggtct    1020
```

```
tggagaattg gatcaagcca taaccatttc ggataccaaa acccaatggc agcatggata    1080
ttatcaaata catctgactt taaaccaaag tcaccaaatg ctgctacaga ttggaataac    1140
agtttaaaga gacaaataga attctatcaa tggttacaat ctgctgaagg tggtatcgct    1200
ggaggagcta gtaactcaaa tggaggaagc tatcaagcat ggccagcagg tactgcaaca    1260
ttctacggaa tgggatatac tcctcaccca gtatacgaag atccaggtag taacgaatgg    1320
tttggtatgc aagcatggtc aatgcaacgt gtggctgaat actactacag ttcaaaagat    1380
ccagcagcta aatcattact tgataaatgg gctaaatggg cttgtgcaaa tgttcaattc    1440
gatgatgcag ctaagaaatt taagattcct gctaaattag tatggactgg acaaccagat    1500
acttggactg gatcatatac aggaaattca aatcttcatg ttaaagttga agcttatgga    1560
gaagatcttg gagtagcagg ttcactttct aatgcattat catattatgc aaaagctctt    1620
gaatctagca cagatgctgc agataaagta gcatataaca ctgcaaaaga aacttctaga    1680
aagatacttg attacttatg ggcaagctac caagatgata agggtatagc agttactgaa    1740
acaagaaatg atttcaaacg tttcaatcaa tctgtatata ttccatcagg ttggacagga    1800
aaaatgccta atggagatgt aatccaaagt ggagctactt tcttaagcat acgttcaaaa    1860
tacaaacaag atccatcatg gccaaaagtt gaagctgctt tagcaaatgg tactggtgtt    1920
gatatgacat accacagatt ctggggtcaa agtgatatcg ctatagcatt tggaacatac    1980
ggtacattat tcacagaccc tactccagga ttaaaaggtg atgttaactc tgatgctaaa    2040
gtaaatgcta tagatttagc tatattaaag aaatacatct tagattcaac aactaaaatt    2100
aacactgcta attctgatat gaacggtgat ggaaaagtta atgcaatgga tttagcttta    2160
ttaaagaaag cacttcttgc ttaa                                          2184

<210> SEQ ID NO 20
<211> LENGTH: 1338
<212> TYPE: DNA
<213> ORGANISM: Clostridium cellulovorans

<400> SEQUENCE: 20
atggaaaagc taagatttcc caaagatttt attttttggaa cagccactgc agcatatcaa     60
attgaaggag cttacaaaga agatgagaaa ggtgaatcta tttgggatag gtttagtcat    120
ataccaggaa atgtagctaa atgcataat ggtgatattg cttgtgatca ctatcataga    180 tataagaag atgttcagct attaaaaagc cttggaatta aagttatag gttttcaatt    240 gcttggccta gaatttttcc caaaaggttt ggcgagataa accagaaggg aattcagttc    300
tatagggatt taattgatga actaattaaa aatgatatag aaccagctat aacaatttat    360
cattgggatc ttccacaaaa gcttcaggat attggagggt gggcaaatcc gcaagttgct    420
gattactatg ttgattatgc aaacttatta ttcagagagt tcggagatag agtaaaaaca    480
tggataactc ataatgagcc atgggttgca tcatatcttg gctatgcttt aggagttcat    540
gctccaggaa ttaaagatat gaaaatggca ttgttagctg cacataacat attattatcg    600
cactttaagg cagttaaagc ttatagaaaa ttagaacaag atgggcaaat aggtataaca    660
ttaaatcttt caacctgtta ttcaaattca gctgatgaag aagatattgc tgcagcccat    720
agaagtgatg gatggaacaa cagatggttt ttagatgctg cattaaaagg aacttatcct    780
gaggatatga taaaaatctt tagcgataca aatattatgc ctgaactacc taagagtta    840 tttactgagg tatttgaaac ttctgatttt ttaggaataa attattatac acgacaagtt    900
```

```
gtaaagaata actctgaagc ttttatcggt gctgaaagtg tagcaatgga taatcctaaa    960
acagaaatgg gttgggagat atatccgcaa gggctttatg atttgctaac gaggatacac   1020
agggattatg ggaacataga tttatacata acagaaaacg gtgcagcttt taatgatatg   1080
gttaatagag acggtaaagt tgaagatgaa aatagattag attatttata cactcatttt   1140
gctgctgcat taagtgctat agaagcggga gtacctttaa agggatatta tatttggtct   1200
ttcatggata attttgagtg ggctgaagga tatgaaaaaa gatttggaat agtacatgta   1260
aactataaaa ctcaggagag aacaataaag aagagtgctt attggtataa ggagcttata   1320
gaaagatcta ataagtaa                                                 1338

<210> SEQ ID NO 21
<211> LENGTH: 84
<212> TYPE: DNA
<213> ORGANISM: artificial sequence
<220> FEATURE:
<223> OTHER INFORMATION: Signal peptide

<400> SEQUENCE: 21
atgcaaaaaa agaaatcgct gaatttattg ttagcattaa tgatggtatt tgctttagta     60
ctaccaagta taccagcttt agca                                            84

<210> SEQ ID NO 22
<211> LENGTH: 486
<212> TYPE: DNA
<213> ORGANISM: artificial sequence
<220> FEATURE:
<223> OTHER INFORMATION: Carbohydrate binding domain

<400> SEQUENCE: 22
gcgacatcat caatgtcagt tgaattttac aactctaaca atcagcaca aacaaactca      60 attacaccaa taatcaaaat tactaacaca tctgacagtg atttaaattt aaatgacgta    120
aaagttagat attattacac aagtgatggt acacaaggac aaactttctg gtgtgaccat    180
gctggtgcat tattaggaaa tagctatgtt gataacacta gcaaagtgac agcaaacttc    240
gttaaagaaa cagcaagccc aacatcaacc tatgatacat atgttgaatt tggatttgca    300
agcggacgag ctactcttaa aaaaggacaa tttataacta ttcaaggaag aataacaaaa    360
tcagactggt caaactacac tcaaacaaat gactattcat ttgatgcaag tagttcaaca    420
ccagttgtaa atccaaaagt tacaggatat ataggtggag ctaaagtact tggtacagca    480
ccaggt                                                              486

<210> SEQ ID NO 23
<211> LENGTH: 27
<212> TYPE: DNA
<213> ORGANISM: artificial sequence
<220> FEATURE:
<223> OTHER INFORMATION: deltaATG-D

<400> SEQUENCE: 23 tttttttgagc tcgcccgggg atcgatc                                        27

<210> SEQ ID NO 24
<211> LENGTH: 40
<212> TYPE: DNA
<213> ORGANISM: artificial sequence
<220> FEATURE:
<223> OTHER INFORMATION: deltaATG-R

<400> SEQUENCE: 24
``` tttttttgagc tcttcaaaat tcctccgaat atttttttac                          40

<210> SEQ ID NO 25
<211> LENGTH: 40
<212> TYPE: DNA
<213> ORGANISM: artificial sequence
<220> FEATURE:
<223> OTHER INFORMATION: ampD

<400> SEQUENCE: 25 tttttttgcta gcaccccctat ttgtttattt ttctaaatac                         40

<210> SEQ ID NO 26
<211> LENGTH: 37
<212> TYPE: DNA
<213> ORGANISM: artificial sequence
<220> FEATURE:
<223> OTHER INFORMATION: ampR

<400> SEQUENCE: 26
ttttttgcta gcgtctgacg ctcagtggaa cgaaaac                              37

<210> SEQ ID NO 27
<211> LENGTH: 37
<212> TYPE: DNA
<213> ORGANISM: artificial sequence
<220> FEATURE:
<223> OTHER INFORMATION: bglA-D

<400> SEQUENCE: 27 tttttttgagc tcatggaaaa gctaagattt cccaaag                             37

<210> SEQ ID NO 28
<211> LENGTH: 39
<212> TYPE: DNA
<213> ORGANISM: artificial sequence
<220> FEATURE:
<223> OTHER INFORMATION: bglA-R

<400> SEQUENCE: 28 tttttttctag attacttatt agatctttct ataagctcc                           39

<210> SEQ ID NO 29
<211> LENGTH: 38
<212> TYPE: DNA
<213> ORGANISM: artificial sequence
<220> FEATURE:
<223> OTHER INFORMATION: engD-D

<400> SEQUENCE: 29 tttttttgagc tcatgattaa acatctatta tcacgggg                            38

<210> SEQ ID NO 30
<211> LENGTH: 39
<212> TYPE: DNA
<213> ORGANISM: artificial sequence
<220> FEATURE:
<223> OTHER INFORMATION: engD-R

<400> SEQUENCE: 30 tttttttgcat gctattttac tgtgcattca gtaccattc                           39

<210> SEQ ID NO 31
<211> LENGTH: 71
<212> TYPE: DNA

<213> ORGANISM: artificial sequence
<220> FEATURE:
<223> OTHER INFORMATION: engD-DRBS

<400> SEQUENCE: 31
tttttttcta gaggtaggta aaaaaatatt cggaggaatt tgaaatgat taaacatcta    60 ttatcacggg g    71

<210> SEQ ID NO 32
<211> LENGTH: 42
<212> TYPE: DNA
<213> ORGANISM: artificial sequence
<220> FEATURE:
<223> OTHER INFORMATION: cbpA-D

<400> SEQUENCE: 32 tttttttgagc tcatgcaaaa aaagaaatcg ctgaatttat tg    42

<210> SEQ ID NO 33
<211> LENGTH: 43
<212> TYPE: DNA
<213> ORGANISM: artificial sequence
<220> FEATURE:
<223> OTHER INFORMATION: mcbpA2C-R

<400> SEQUENCE: 33 tttttttctag attattctag tataggatct ccaatattta ttg    43

<210> SEQ ID NO 34
<211> LENGTH: 61
<212> TYPE: DNA
<213> ORGANISM: artificial sequence
<220> FEATURE:
<223> OTHER INFORMATION: mcbpA2CHT-R

<400> SEQUENCE: 34 tttttttctag attagtgatg atgatgatga tgttctagta taggatctcc aatatttatt    60
g    61

<210> SEQ ID NO 35
<211> LENGTH: 504
<212> TYPE: DNA
<213> ORGANISM: artificial sequence
<220> FEATURE:
<223> OTHER INFORMATION: SLH 1 of engE

<400> SEQUENCE: 35
gcagaagcta actacacaac aaaaggcact acgacacaga tatatcttag tgcctttgca    60
caaaatactg atgactgggc ttggatgagt atgggagata ctgctagctt agtatatcaa    120
gacgtaacaa atttcaatgc catcgacgct actagtgcct ttgcaaaggc aaatggtact    180
gcaaactttg ggttacaggt tgttgatgga atcttgctg caggagaaaa aagtacatta    240
aaattccata ttgaacagt tactattaaa gcaactggat ataatgatgt tgtggttaat    300
cttaacaagg attattcaga agcatatgca gcagaaaaag tttcttgggg aatcacagga    360
aacaatacat caattttact aaatgattat ttaccaacag atgcagcagc gaaagcaacg    420
tatctacaaa agattactag tgtaaaagca gatgttacat tatcagaata tcaatttgtt    480
aaaccagcat caactgggtc aact    504

<210> SEQ ID NO 36
<211> LENGTH: 498

```
<212> TYPE: DNA
<213> ORGANISM: artificial sequence
<220> FEATURE:
<223> OTHER INFORMATION: SLH 2 of engE

<400> SEQUENCE: 36
tctgaaagtg tatactcatc aggtgatgca acaaagattt atgctagtgc gtttgcacaa      60
aatactgatg actgggcttg gatgagcatg ggagatactg ctgttttaac atatcaaact     120
gctacaaacg taaatgctat caatgcaggt actgcatttg caagtgcaaa tggaactgca     180
aactttggta tccaaattgt tgacggaaac ctagctgctg caggagactc aagtacatta     240
aaattccatg ttggaacagt tacaattaaa gcaacaggtt atgatgatct tgtagttgct     300
ctaaataaag attattcaga agcatatact gcagaaaaaa tgacttgggg acttactgga     360
aataacacac aaattttatt aaatagttat ttaccaacgg atgcaactgc aaaagctgca     420
tatctacaaa aataacttc tgttacagct gatgttacag taacagatta tcaatcgatt       480
aaaccagcaa cagcaact                                                    498

<210> SEQ ID NO 37
<211> LENGTH: 561
<212> TYPE: DNA
<213> ORGANISM: artificial sequence
<220> FEATURE:
<223> OTHER INFORMATION: SLH 3 of engE

<400> SEQUENCE: 37
ggggaagttc tttacacaac accaggtgtt gaaacaaaga tttctgctag tgcttttgca      60
caaaacaccg atgactgggc ttggatgagc gtaggtgatg gtgttagtct tcaatatcaa     120
actgatacaa ctttaaatgc tattagtgct gctggtacat tagcaaaagc aaatgctaca     180
gcaaactttg gtataaatat tgttgatgga atcttgctg ctggagatgc aaacacatta      240
aagttccatg ttggaacagt tacaattaaa gcaacaggtt atgatgacct tgtgattaac     300
ttaaataaag attattcaga agcatttgca gcagaaaaag cttcttgggg acttacagga     360
aacacaaaac aaattttatt aaactcttat ttaccaacag atgcaacagc aaaagtaaac     420
tatcttcaaa aggttactag tgttacagct gatgtaaaag taacagatta tacgtttatt     480
aaatatgtac caccagcacc agaattccct gctgattaca ctcacccaac agaaatgaga     540
ggtctttctg ctatggattt a                                                561

<210> SEQ ID NO 38
<211> LENGTH: 159
<212> TYPE: DNA
<213> ORGANISM: artificial sequence
<220> FEATURE:
<223> OTHER INFORMATION: dockerin domain of engE

<400> SEQUENCE: 38
ggcgatgtag acggtaatga tgtagttaat tcacttgatt tgagttatt aaagaagtat       60 gtattaaaca atgatacaat gataaacaaa gctagtgcag atttaaataa ggatggaaaa     120
atcaacataa ttgatcttgc attcttaaaa aaagcaata                             159

<210> SEQ ID NO 39
<211> LENGTH: 168
<212> TYPE: DNA
<213> ORGANISM: artificial sequence
<220> FEATURE:
<223> OTHER INFORMATION: dockerin domain of engH
```

```
<400> SEQUENCE: 39
ggtgatgtaa  acaataatgg  tatcgtgaat  tcaatggatt  tagcgatgtt  aaagaaatat    60
atacttggat  acgaagtaga  atgaataaaa  gaggcttcag  atttaaataa  agatggtaag   120
attaatgcca  ttgatttcgc  tcttttaaag  aaactacttt  tatcacag                168

<210> SEQ ID NO 40
<211> LENGTH: 186
<212> TYPE: DNA
<213> ORGANISM: artificial sequence
<220> FEATURE:
<223> OTHER INFORMATION: dockerin domain of engZ

<400> SEQUENCE: 40
ggtgatgtta  ataatgatac  aaagatatct  gccatggatc  ttgcactact  gaagaaacat    60
attatgggta  cctcaacctt  aacaggagat  gcatttacag  cagcagatgt  agattcaaat   120
gggaaagtaa  attcaataga  tttagcttta  ttgaaaaaat  acattttagg  tcaaataact   180
agtttc                                                                  186

<210> SEQ ID NO 41
<211> LENGTH: 156
<212> TYPE: DNA
<213> ORGANISM: artificial sequence
<220> FEATURE:
<223> OTHER INFORMATION: dockerin domain of exgS

<400> SEQUENCE: 41
gatgttaact  ctgatgctaa  agtaaatgct  atagatttag  ctatattaaa  gaaatacatc    60
ttagattcaa  caactaaaat  taacactgct  aattctgata  tgaacggtga  tggaaaagtt   120
aatgcaatgg  atttagcttt  attaaagaaa  gcactt                              156

<210> SEQ ID NO 42
<211> LENGTH: 2988
<212> TYPE: DNA
<213> ORGANISM: artificial sequence
<220> FEATURE:
<223> OTHER INFORMATION: r-cbpASLH4

<400> SEQUENCE: 42
atgcaaaaaa  agaaatcgct  gaatttattg  ttagcattaa  tgatggtatt  tgctttagta    60
ctaccaagta  taccagcttt  agcagcgaca  tcatcaatgt  cagttgaatt  ttacaactct   120
aacaaatcag  cacaaacaaa  ctcaattaca  ccaataatca  aaattactaa  cacatctgac   180
agtgatttaa  atttaaatga  cgtaaaagtt  agatattatt  acacaagtga  tggtacacaa   240
ggacaaactt  tctggtgtga  ccatgctggt  gcattattag  aaatagcta   tgttgataac   300 actagcaaag  tgacagcaaa  cttcgttaaa  gaaacagcaa  gcccaacatc  aacctatgat   360
acatatgttg  aatttggatt  tgcaagcgga  cgagctactc  ttaaaaaagg  acaattttata   420 actattcaag  gaagaataac  aaaatcagac  tggtcaaact  acactcaaac  aaatgactat   480
tcatttgatg  caagtagttc  aacaccagtt  gtaaatccaa  aagttacagg  atatataggt   540
ggagctaaag  tacttggtac  agcaccaggt  ccagatgtac  catcttcaat  aattaatcct   600
acttctgcaa  catttgataa  aaatgtaact  aaacaagcag  atgttaaaac  tactatgact   660
ttaaatggta  acacatttaa  aacaattaca  gatgcaaacg  gtacagctct  aaatgcaagc   720
actgattata  gtgtttctgg  aaatgatgta  acaataagca  aagcttattt  agcaaaacaa   780
tcagtaggaa  caactacatt  aaactttaac  tttagtgcag  gaaatcctca  aaaattagta   840
```

```
attacagtag ttgacacacc agttgaagct gtaacagcta caattggaaa agtacaagta     900
aatgctggag aaacggtagc agtaccagtt aacttaacaa aagttccagc agctggttta     960
gcaacaattg aattaccatt aacttttgat tctgcatcat tagaagtagt atcaataact    1020
gctggagata tcgtattaaa tccatcagta aacttctctt ctacagtaag tggaagcaca    1080
ataaaattat tattcttaga tgatacatta ggaagccaat taatcactaa ggatggagtt    1140
tttgcaacaa taacatttaa agcaaaagct ataactggaa caactgcaaa agtaacttca    1200
gttaaattag ctggaacacc agtagttggt gatgcgcaat tacaagaaaa accttgtgca    1260
gttaacccag aacagtaac tatcaatcca atcgataata aatgcaaat ttcagttgga      1320
acagcaacag taaaagctgg agaaatagca gcagtgccag taacattaac aagtgttcca    1380
tcaactggaa tagcaactgc tgaagcacaa gtaagttttg atgcaacatt attagaagta    1440
gcatcagtaa ctgctggaga tatcgtatta aatccaacag taaacttctc ttatacagta    1500
aacggaaatg taataaaatt attattccta gatgatacat taggaagcca attaattagt    1560
aaagatggag tttttgtaac aataaacttc aaagcaaaag ctgtaacaag cacagtaaca    1620
acaccagtta cagtatcagg aacacctgta tttgcagatg gtacattagc agaagtacaa    1680
tctaaaacag cagcaggtag cgttacaata aatattggag atcctatact agaaccaaca    1740
ataagccctg taactgcaac ttttgataaa aaagcaccag cagacgttgc aacaacaatg    1800
acattaaatg gttatacatt taacggaatc acaggattaa caacatcaga ctacagtatt    1860
tcaggtaatg tagtgaaaat tagccaagca tatttagcta acaaccagt tggagatctt     1920
acattaacat ttaacttctc aaatggtaat aaaactgcaa cagctaaatt agtagtatca    1980
atcaaagatg caccaaaaac tacagtagct ccaacagctg taacatttga taagctaat    2040
caagcagatg ctgcaataac aatgacatta aacggaaaca cattctcagc aataaagaat    2100
ggaacagcta cattagtaaa aggaactgat tacacagttt cagaaaatgt agtaacaatc    2160
agcaaagctt acttagctaa gcaaactgga acagttacat tagaatttgt atttgacaaa    2220
ggaaattcag ctaaagttgt tgtagctgta aaagaaattc aaattgtaaa ttcaacaata    2280
actccagtag tagcaacatt tgaaaaaact gctgctaaac aagcagatgt tgtagtaaca    2340
atgtctttaa atggtaacac attctcagca ataagaatg gaacaactac attagtaaaa    2400
ggaactgatt acacaatttc aggaagcaca gtaacaatca gcaaagctta cctagctaca    2460
ttagcagatg gaagtgcaac attagaattt gtatttaacc aagggctag tgcaaaatta    2520
cgattaacta tagtaccagc agtagtagat ccagtagtaa ctgattttgc tgttaaaatt    2580
gacaaagtat ctgcagcagc aggttctaca gttaaagttc cagtatcatt aattaatgtt    2640
tctaaggtt gaaatgtttg tgtagctgaa tacaaaatca gctttgactc aagtgtactt     2700
acatatgtag aactacagc aggaacatca atcaaaaatc ctgcagttaa cttctcatca     2760
caacttaacg aaacactat tacattatta ttctttgaca atacaattgg aaatgaatta    2820
ataacagctg atggtcaatt cgctacaatc gaattcaaag ttaatgcagc agctacttca    2880
ggaacaactg cagaagttaa agtagcaact ataagctcat tcgctgatgc atcattaact    2940
gaaatcacta agtagctac agttaacgga agtgttaaag ttagctaa                  2988
```

<210> SEQ ID NO 43
<211> LENGTH: 3567
<212> TYPE: DNA
<213> ORGANISM: artificial sequence
<220> FEATURE:

<223> OTHER INFORMATION: r-cbpASLHE

<400> SEQUENCE: 43

```
atgcaaaaaa agaaatcgct gaatttattg ttagcattaa tgatggtatt tgctttagta      60
ctaccaagta taccagcttt agcagcgaca tcatcaatgt cagttgaatt ttacaactct     120
aacaaatcag cacaaacaaa ctcaattaca ccaataatca aaattactaa cacatctgac     180
agtgatttaa atttaaatga cgtaaaagtt agatattatt acacaagtga tggtacacaa     240
ggacaaactt tctggtgtga ccatgctggt gcattattag gaaatagcta tgttgataac     300
actagcaaag tgacagcaaa cttcgttaaa gaaacagcaa gcccaacatc aacctatgat     360
acatatgttg aatttggatt tgcaagcgga cgagctactc ttaaaaaagg acaatttata     420
actattcaag gaagaataac aaaatcagac tggtcaaact acactcaaac aaatgactat     480
tcatttgatg caagtagttc aacaccagtt gtaaatccaa aagttacagg atatataggt     540
ggagctaaag tacttggtac agcaccaggt ccagatgtac catcttcaat aattaatcct     600
acttctgcaa catttgataa aaatgtaact aaacaagcag atgttaaaac tactatgact     660
ttaaatggta acacatttaa aacaattaca gatgcaaacg gtacagctct aaatgcaagc     720
actgattata gtgtttctgg aaatgatgta acaataagca aagcttattt agcaaaacaa     780
tcagtaggaa caactacatt aaactttaac tttagtgcag gaaatcctca aaaattagta     840
attacagtag ttgacacacc agttgaagct gtaacagcta caattggaaa agtacaagta     900
aatgctggag aaacggtagc agtaccagtt aacttaacaa agttccagc agctggttta     960
gcaacaattg aattaccatt aacttttgat tctgcatcat tagaagtagt atcaataact    1020
gctggagata tcgtattaaa tccatcagta aacttctctt ctacagtaag tggaagcaca    1080
ataaaattat tattcttaga tgatacatta ggaagccaat taatcactaa ggatggagtt    1140
tttgcaacaa taacatttaa agcaaaagct ataactggaa caactgcaaa agtaacttca    1200
gttaaattag ctggaacacc agtagttggt gatgcgcaat tacaagaaaa accttgtgca    1260
gttaacccag gaacagtaac tatcaatcca atcgataata gaatgcaaat ttcagttgga    1320
acagcaacag taaaagctgg agaaatagca gcagtgccag taacattaac aagtgttcca    1380
tcaactggaa tagcaactgc tgaagcacaa gtaagttttg atgcaacatt attagaagta    1440
gcatcagtaa ctgctggaga tatcgtatta aatccaacag taaacttctc ttatacagta    1500
aacggaaatg taataaaatt attattccta gatgatacat taggaagcca attaattagt    1560
aaagatggag tttttgtaac aataaacttc aaagcaaaag ctgtaacaag cacagtaaca    1620
acaccagtta cagtatcagg aacacctgta tttgcagatg gtacattagc agaagtacaa    1680
tctaaaacag cagcaggtag cgttacaata aatattggag atcctatact agaaccaaca    1740
ataagccctg taactgcaac ttttgataaa aaagcaccag cagacgttgc aacaacaatg    1800
acattaaatg gttatacatt taacggaatc acaggattaa caacatcaga ctacagtatt    1860
tcaggtaatg tagtgaaaat tagccaagca tatttagcta acaaccagt tggagatctt    1920
acattaacat taacttctc aaatggtaat aaaactgcaa cagctaaatt agtagtatca    1980
atcaaagatg caccaaaaac tgcagaagct aactacacaa caaaggcac tacgacacag    2040
atatatctta gtgcctttgc acaaaatact gatgactggg cttggatgag tatgggagat    2100
actgctagct tagtatatca agacgtaaca aatttcaatg ccatcgacgc tactagtgcc    2160
tttgcaaagg caaatggtac tgcaaacttt ggcttacagg ttgttgatgg aaatcttgct    2220
gcaggagaaa aaagtacatt aaaattccat attggaacag ttactattaa agcaactgga    2280
```

```
tataatgatg ttgtggttaa tcttaacaag gattattcag aagcatatgc agcagaaaaa    2340
gtttcttggg gaatcacagg aaacaataca tcaattttac taaatgatta tttaccaaca    2400
gatgcagcag cgaaagcaac gtatctacaa aagattacta gtgtaaaagc agatgttaca    2460
ttatcagaat atcaatttgt taaaccagca tcaactgggt caacttctga agtgtatac     2520 tcatcaggtg atgcaacaaa gatttatgct agtgcgtttg cacaaaatac tgatgactgg    2580
gcttggatga gcatgggaga tactgctgtt ttaacatatc aaactgctac aaacgtaaat    2640
gctatcaatg caggtactgc atttgcaagt gcaaatggaa ctgcaaactt tggtatccaa    2700
attgttgacg gaaacctagc tgctgcagga gactcaagta cattaaaatt ccatgttgga    2760
acagttacaa ttaaagcaac aggttatgat gatcttgtag ttgctctaaa taagattat     2820 tcagaagcat atactgcaga aaaaatgact tggggactta ctggaaataa cacacaaatt    2880
ttattaaata gttatttacc aacggatgca actgcaaaag ctgcatatct acaaaaaata    2940
acttctgtta cagctgatgt tacagtaaca gattatcaat cgattaaacc agcaacagca    3000
actggggaag ttctttacac aacaccaggt gttgaaacaa agatttctgc tagtgctttt    3060 gcacaaaaaca ccgatgactg gcttggatg agcgtaggtg atggtgttag tcttcaatat    3120
caaactgata caactttaaa tgctattagt gctgctggta cattagcaaa agcaaatgct    3180
acagcaaact ttggtataaa tattgttgat ggaaatcttg ctgctggaga tgcaaacaca    3240
ttaaagttcc atgttggaac agttacaatt aaagcaacag gttatgatga ccttgtgatt    3300
aacttaaata aagattactc agaagcattt gcagcagaaa aagcttcttg gggacttaca    3360
ggaaacacaa aacaaatttt attaaactct tatttaccaa cagatgcaac agcaaaagta    3420
aactatcttc aaaaggttac tagtgttaca gctgatgtaa aagtaacaga ttatacgttt    3480
attaaatatg taccaccagc accagaattc cctgctgatt acactcaccc aacagaaatg    3540
agaggtcttt ctgctatgga tttataa                                        3567
```

<210> SEQ ID NO 44
<211> LENGTH: 2069
<212> TYPE: DNA
<213> ORGANISM: artificial sequence
<220> FEATURE:
<223> OTHER INFORMATION: r-cbpA-I

<400> SEQUENCE: 44

```
atgcaaaaaa agaaatcgct gaatttattg ttagcattaa tgatggtatt tgctttagta     60
ctaccaagta taccagcttt agcagcgaca tcatcaatgt cagttgaatt ttacaactct    120
aacaaatcag cacaaacaaa ctcaattaca ccaataatca aaattactaa cacatctgac    180
agtgatttaa atttaaatga cgtaaaagtt agatattatt acacaagtga tggtacacaa    240
ggacaaactt tctggtgtga ccatgctggt gcattattag gaaatagcta tgttgataac    300
actagcaaag tgacagcaaa cttcgttaaa gaaacagcaa gcccaacatc aacctatgat    360
acatatgttg aatttggatt tgcaagcgga gcagctactc ttaaaaaagg acaatttata    420
actattcaag gaagaataac aaaatcagac tggtcaaact acactcaaac aaatgactat    480
tcatttgatg caagtagttc aacaccagtt gtaaatccaa agttacagg atatataggt    540 ggagctaaag tacttggtac agcaccaggt ccagatgtac catcttcaat aattaatcct    600
acttctgcaa catttgataa aaatgtaact aaacaagcag atgttaaaac tactatgact    660
ttaaatggta acacatttaa aacaattaca gatgcaaacg gtacagctct aaatgcaagc    720
```

```
actgattata gtgtttctgg aaatgatgta acaataagca aagcttattt agcaaaacaa    780
tcagtaggaa caactacatt aaactttaac tttagtgcag gaaatcctca aaaattagta    840
attacagtag ttgacacacc agttgaagct gtaacagcta caattggaaa agtacaagta    900
aatgctggag aaacggtagc agtaccagtt aacttaacaa agttccagc agctggttta     960 gcaacaattg aattaccatt aacttttgat tctgcatcat tagaagtagt atcaataact   1020
gctggagata tcgtattaaa tccatcagta aacttctctt ctacagtaag tggaagcaca   1080
ataaaattat tattcttaga tgatacatta ggaagccaat taatcactaa ggatggagtt   1140
tttgcaacaa taacatttaa agcaaaagct ataactggaa caactgcaaa agtaacttca   1200
gttaaattag ctggaacacc agtagttggt gatgcgcaat tacaagaaaa accttgtgca   1260
gttaacccag gaacagtaac tatcaatcca atcgataata gaatgcaaat ttcagttgga   1320
acagcaacag taaaagctgg agaaatagca gcagtgccag taacattaac aagtgttcca   1380
tcaactggaa tagcaactgc tgaagcacaa gtaagttttg atgcaacatt attagaagta   1440
gcatcagtaa ctgctggaga tatcgtatta atccaacag taaacttctc ttatacagta    1500
aacggaaatg taataaaatt attattccta gatgatacat taggaagcca attaattagt   1560
aaagatggag tttttgtaac aataaacttc aaagcaaaag ctgtaacaag cacagtaaca   1620
acaccagtta cagtatcagg aacacctgta tttgcagatg gtacattagc agaagtacaa   1680
tctaaaacag cagcaggtag cgttacaata aatattggag atcctatact agaaccaaca   1740
ataagccctg taactgcaac ttttgataaa aaagcaccag cagacgttgc aacaacaatg   1800
acattaaatg gttatacatt taacggaatc acaggattaa caacatcaga ctacagtatt   1860
tcaggtaatg tagtgaaaat tagccaagca tatttagcta acaaccagt tggagatctt    1920 acattaacat ttaacttctc aaatggtaat aaaactgcaa cagctaaatt agtagtatca   1980
atcaaagatg caccaaaaac tacagtagct ccaacagctg taacggaagt gttaaagtta   2040
gccatcatca tcatcatcac taatctaga                                     2069
```

<210> SEQ ID NO 45
<211> LENGTH: 81
<212> TYPE: DNA
<213> ORGANISM: artificial sequence
<220> FEATURE:
<223> OTHER INFORMATION: Signal peptide of L. lactis Usp45

<400> SEQUENCE: 45

```
atgaaaaaaa agattatctc agctatttta atgtctacag tgatactttc tgctgcagcc    60
ccgttgtcag gtgtttatgc a                                              81
```

<210> SEQ ID NO 46
<211> LENGTH: 27
<212> TYPE: DNA
<213> ORGANISM: artificial sequence
<220> FEATURE:
<223> OTHER INFORMATION: deltaXho-D

<400> SEQUENCE: 46

```
tttttttctcg agctcgcccg gggatcg                                       27
```

<210> SEQ ID NO 47
<211> LENGTH: 41
<212> TYPE: DNA
<213> ORGANISM: artificial sequence
<220> FEATURE:
<223> OTHER INFORMATION: deltaXho-R

<400> SEQUENCE: 47 tttttttctcg agttcaaaat tcctccgaat aatttttta c          41

<210> SEQ ID NO 48
<211> LENGTH: 27
<212> TYPE: DNA
<213> ORGANISM: artificial sequence
<220> FEATURE:
<223> OTHER INFORMATION: cbpA-SLH4-R1

<400> SEQUENCE: 48 agttttggt gcatctttga ttgatac                           27

<210> SEQ ID NO 49
<211> LENGTH: 55
<212> TYPE: DNA
<213> ORGANISM: artificial sequence
<220> FEATURE:
<223> OTHER INFORMATION: cbpA-SLH4-D2

<400> SEQUENCE: 49
gtatcaatca aagatgcacc aaaaactaca gtagctccaa cagctgtaac atttg    55

<210> SEQ ID NO 50
<211> LENGTH: 38
<212> TYPE: DNA
<213> ORGANISM: artificial sequence
<220> FEATURE:
<223> OTHER INFORMATION: cbpA-R

<400> SEQUENCE: 50 tttttctag attagctaac tttaacactt ccgttaac               38

<210> SEQ ID NO 51
<211> LENGTH: 58
<212> TYPE: DNA
<213> ORGANISM: artificial sequence
<220> FEATURE:
<223> OTHER INFORMATION: cbpA-RH

<400> SEQUENCE: 51 tttttctag attagtgatg atgatgatga tggctaactt taacacttcc gttaactg   58

<210> SEQ ID NO 52
<211> LENGTH: 52
<212> TYPE: DNA
<213> ORGANISM: artificial sequence
<220> FEATURE:
<223> OTHER INFORMATION: engESLH-D

<400> SEQUENCE: 52
gtatcaatca aagatgcacc aaaaactgca gaagctaact acacaacaaa ag       52

<210> SEQ ID NO 53
<211> LENGTH: 39
<212> TYPE: DNA
<213> ORGANISM: artificial sequence
<220> FEATURE:
<223> OTHER INFORMATION: engESLH-R2

<400> SEQUENCE: 53 tttttctag attataaatc catagcagaa agacctctc              39

RECOMBINANT CELLULOSOME COMPLEX AND USES THEREOF

CROSS-REFERENCE TO RELATED APPLICATION

This application is the U.S. national stage application of International Patent Application No. PCT/EP2013/061413, filed Jun. 3, 2013.

The Sequence Listing for this application is labeled "Seq-List.txt" which was created on Dec. 1, 2014 and is 52 KB. The entire contents of the sequence listing is incorporated herein by reference in its entirety.

The present invention relates to an improved cellulase system, also called cellulosome, derived from a cellulolytic bacterium. The present invention further relates to the use of such improved cellulase system for modifying a lactic acid bacterium so that such recombinant bacterium may degrade cellulose, including crystalline cellulose. More particularly, the invention relates to a recombinant lactic acid bacterium expressing an improved cellulase system and producing lactic acid from cellulosic biomass. The present invention further relates to methods for degrading a cellulosic biomass using said recombinant lactic acid bacterium, and advantageously producing lactic acid.

CONTEXT OF THE INVENTION

Cellulose is the most abundant biomass on Earth and the largest waste produced by human activities, including agro-industrial by-products (e.g., wheat straw and corn stalks), municipal solid wastes (e.g. waste paper) and industrial waste stream (e.g., paper mill sludge). For this reason, cellulosic biomass is the most attractive substrate for biorefinery strategies that produce high-value products (e.g., chemicals, fuels, bioplastics, enzymes) through fermentation processes.

The use of microorganisms to conduct modification of cellulosic biomass for the production of products of interest has been proposed in the art. However, up to now, the cellulosic biomass bioconversion processes are economically inefficient multistep processes. Indeed, a pre-treatment, which converts cellulosic biomass from its native form to a form that is less recalcitrant to enzymatic biodegradation, is generally required. Furthermore, all process configurations require dedicated cellulase production. The bioconversion of cellulosic biomass into high-value products includes four biologically mediated events: 1) cellulase production; 2) the hydrolysis of cellulose and (if present) other insoluble polysaccharides (e.g., hemicellulose); 3) the fermentation of glucose and other soluble cellulose hydrolysis products; and 4) the fermentation of soluble hemicellulose hydrolysis products.

Research efforts have been aimed at developing recombinant microorganisms that have the characteristics required for biomass consolidated bioprocessing. The heterologous expression of extracellular proteins (e.g., cellulase or hemicellulase) is the key feature of recombinant cellulolytic strategies, because it confers cellulolytic ability to microorganisms with high-value product formation properties.

Lactic acid bacteria are among the most promising microorganisms for biorefineries (Berlec et al., 2009 Recent Pat Biotechnol. 3(2):77-87). They are robust organisms already adapted to industrial process stressing conditions which show high acid tolerance, which makes them able to survive to pH 5 and lower, and broad optimal temperature for growth, which varies from 20 to 45° C., depending on the genus and strain (Hofvendahl et al., 2000 Enzyme Microb Technol. 26(2-4):87-107). Apart from their current main application as food starters (e.g., for dairy products, pickles, meat and wine), lactic acid bacteria produce a large spectrum of high-value molecules such as bacteriocins, whose antimicrobial properties have been employed for pathogenic and/or food spoilage bacteria (e.g., *Listeria monocytogenes* and *Staphylococcus aureus*) or inhibition (Settanni et al., 2008 Int. J. Food. Microbiol. 121(2):123-38; Fadda et al., 2010 Meat Sci. 2010, 86(1): 66-79); food aromas such as diacetyl and acetaldehyde (Hugenholtz et al., 2011, Rotterdam, The Netherlands: Media Labs, 113-132); vitamins (e.g., folate and vitamin B12) (Hugenholtz et al., 2011); exopolysaccharides, which are important for food texture and as prebiotics (Hugenholtz et al., 2011); nutraceutical molecules such as γ-amino butyric acid (GABA), a bioactive molecule with beneficial effects for human health (Mazzoli et al., 2010, Amino Acids 39: 727-737) or Se-metabolites (Lamberti et al., 2011, Proteomics. 11(11):2212-21). Lactic acid bacteria are able to catabolize a high number of mono- (both hexose and pentose) and di-saccharides through different metabolic pathways resulting in homo-, hetero- and mixed acid fermentation phenotype.

Lactic acid, the main fermentation product produced by lactic acid bacteria, is currently among the most valuable chemicals because of its use as a building block for the synthesis of polymers, particularly polylactide (PLA), which can be used as a biodegradable and biocompatible general-purpose plastic material, and the increasing demand for ethyl lactate, which is used as a biodegradable solvent (Singh et al., 2007, J. Nanosci. Nanotechnol. 7(8): 2596-615; Madhavan Nampoothiri et al., 2010 Bioresour. Technol. 101(22): 8493-501). Heterofermentative and mixed acid fermentative produce other high added value molecules.

Ethanol is a highly esteemed biofuel and solvent. Formate can be used for hydrogen production through formate hydrogen lyase (FHL) (Levin et al., 2009, Int. J. Hydrogen Energy 34: 7390-7403).

Moreover, some lactic acid bacteria are able to accumulate polyhydroxyalkanoates (PHA) with huge potential for application as biodegradable plastics (Aslim et al., 1998, FEMS Microbiol Lett 159: 293-7).

Up to now, the process for converting cellulosic biomass into lactic acid is not feasible due to the high cost of enzymes involved in cellulose hydrolysis. Although many molecular tools are available, one of the main challenges of metabolic pathway engineering is to find an efficient heterologous cellulase secretion method to allow recombinant lactic acid bacteria to degrade cellulosic biomass.

Some cellulolytic microorganisms use cellulosomes, which are intricate multi-enzyme complexes, to degrade cellulose and hemicellulose. Cellulosomes are capable of degrading plant cell wall polysaccharides, such as cellulose. A cellulosome comprises a usually non-catalytic polypeptide, called a scaffolding polypeptide, which may help secure and organize cellulolytic enzymes into a complex. In particular, the cellulose-binding domain of the scaffolding polypeptide mediates attachment of the cellulosome to its substrate. The cellulosome may contain as many as 100 or more enzymatic and non-enzymatic components.

Architecture, catalytic composition and mechanisms of attachment to the cell and to cellulose may give some advantage in degrading cellulose efficiently in nature.

By conducting experiments and researches on cellulosomes, the inventors have surprisingly demonstrated that a highly effective synthetic cellulosome, or mini-cellulosome, may be engineered that contains a limited number of enzymatic subunits and exhibits a strong degrading activity, both with regard to soluble and crystalline cellulose. Furthermore, the inventors have shown that such a mini-cellulosome may be efficiently used to modify a lactic acid bacterium so that the resulting recombinant bacterium shows a cellulolytic phenotype. Such recombinant lactic acid bacteria can be advantageously used in a process of degradation of a cellulosic biomass, and notably for producing lactic acid.

SUMMARY OF THE INVENTION

The present invention deals therefore with the development of an optimized recombinant cellulosome, containing a scaffolding polypeptide suitable for anchoring and/or organizing enzymes able to cooperate and degrade crystalline cellulose. The present invention further proposes to use a set of cellulosomal or non-cellulosomal enzymes together with the recombinant scaffolding polypeptide, which contains preferably at least an endoglucanase, an exoglucanase and a β-glycosidase, efficient for degrading crystalline cellulose. In addition, the present invention relates to recombinant lactic acid bacteria that contain a minicellulosome of the invention. Such bacteria are able to hydrolyze crystalline cellulose and to ferment cellulose hydrolysis products into lactic acid. Such recombinant cellulolytic lactic acid bacteria support single-step fermentation of cellulose into lactic acid. The recombinant cellulolytic lactic acid bacteria of the invention may be used to degrade cellulosic biomass and/or to produce lactic acid from cellulosic biomass.

In this regard, an object of the invention relates to an isolated polynucleotide encoding a recombinant scaffolding polypeptide, preferably comprising at least a signal peptide, a Cellulose Binding Domain, two cohesin domains and an S-layer Homology domain.

A further object of the invention relates to a polypeptide comprising at least a Cellulose Binding Domain, two cohesin domains and an S-layer Homology domain, the polypeptide comprising typically from 2 to 8 cohesin domains, preferably from 2 to 7, from 2 to 6, or from 2 to 5 cohesin domains. Preferably, the polypeptide further comprises a signal peptide. The at least 2 cohesin domains may be identical or different from each other.

A further object of the invention relates to a vector comprising a polynucleotide as described above. In a particular embodiment, the vector further encodes an enzyme, in particular a cellulosomal enzyme.

A further object of the invention relates to a recombinant bacterium transformed with or comprising the polynucleotide or vector as described above. Preferably, the bacterium encodes the scaffolding polypeptide of the invention as well as at least one enzyme, preferably a cellulosomal enzyme.

A further object of the invention relates to a recombinant lactic acid bacterium, wherein said bacterium expresses
  a recombinant scaffolding polypeptide comprising at least
    a signal peptide, a Cellulose Binding Domain, two cohesin domains and an S-layer Homology domain, and optionally
  at least a recombinant endoglucanase suitable for binding the recombinant scaffolding protein through a cohesin domain, and/or
  at least a recombinant exoglucanase suitable for binding the recombinant scaffolding protein through another cohesin domain, and/or
  a recombinant β-glycosidase.

A further object of the invention relates to a method for degrading a cellulosic biomass using a recombinant lactic acid bacterium as described above.

A further object of the invention relates to a method for producing lactic acid from a cellulosic biomass using a recombinant lactic acid bacterium as described above.

A further object of the invention relates to a fermentation tank, such as a bioreactor or a chemostat, comprising a cellulosic biomass, and a recombinant lactic acid bacterium as described above.

The invention also relates to the use of a recombinant lactic acid bacterium as described above for degrading cellulosic biomass or cellulose, particularly crystalline cellulose.

DETAILED DESCRIPTION OF THE INVENTION

Figure 1:
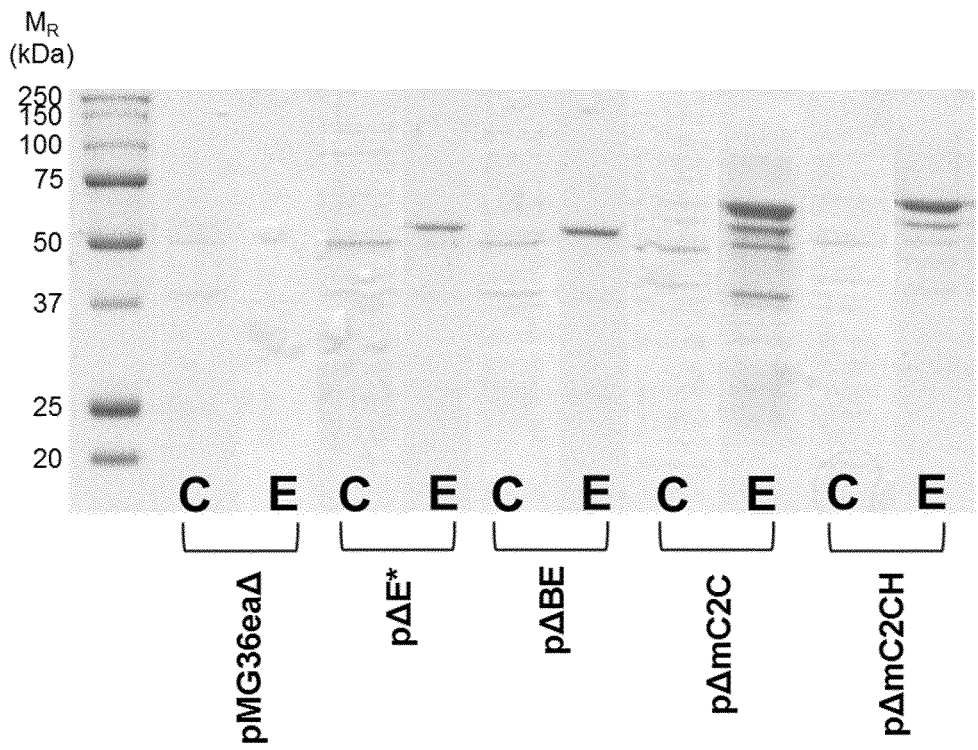
FIG. 1. SDS-PAGE of cellulose-bound proteins present in the cellular (C) and extracellular (E) fractions of *L. lactis* (pMG36eaΔ), *L. lactis* (pΔE)*, *L. lactis* (pΔBE),) *L. lactis* (pΔmC2C) and *L. lactis* (pΔmC2CH)

The present invention relates to the development of an efficient mini-cellulosome, as well as to the uses thereof, particularly for modifying bacteria such as lactic acid bacteria. The invention surprisingly shows that a scaffolding polypeptide can be engineered and produced which allows degradation of cellulose by cooperative reaction with different types of enzymes, e.g., a cellulosomal endoglucanase, a cellulosomal exoglucanase and a non-cellulosomal β-glycosidase. In addition, the invention shows that such a mini-cellulosome can be built or expressed in lactic acid bacteria, thereby creating improved and remarkable bacteria exhibiting both the efficiency of a potent cellulosome complex and the capacity to produce lactic acid.

The following is a description of the present invention, including preferred embodiments thereof given in general terms. The present invention is further exemplified in the disclosure given under the heading "Experimentations" herein below, which provides experimental data supporting the invention, and means of performing the invention.

DEFINITIONS

The present disclosure will be best understood by reference to the following definitions.

Within the context of the invention, a "cellulosome complex" refers to a multi-enzyme system comprising at least a scaffolding polypeptide or subunit and several catalytic subunits containing a dockerin domain suitable for anchoring the cohesin modules of the scaffolding subunit. A cellulosome complex is extracellular, and is preferentially attached to the cell wall of a microorganism. Currently known cellulosome-producing bacteria include *Acetivibrio cellulolyticus*, *Bacteroides cellulosolvens*, *Clostridium acetobutylicum*, *Clostridium cellulolyticum*, *Clostridium*

*cellulovorans, Clostridium josui, Clostridium papyrosolvens, Clostridium thermocellum* and *Ruminococcus flavefaciens*. Natural cellulosome complexes generally involve a scaffolding protein containing multiple cohesin modules, a cellulose binding module and cell surface binding domain(s) (one or more S-layer homology modules or sortase recognition motifs). The term "scaffolding" polypeptide is known in the art and designates a structural polypeptide which forms a complex structure allowing efficient interaction and cooperation of enzymes and substrates.

The term "cellulosic biomass" according to the invention designates a (raw) biomass containing soluble and/or crystalline cellulose. The term cellulosic biomass typically includes unprocessed material of vegetal origin. Examples of cellulosic biomass include wood or vegetal material derived from numerous types of plants (corn stover, soybean, wheat straw, switchgrass, sorghum, etc.), and a variety of tree species.

In the present description, the terms "nucleic acid", "nucleic sequence", "polynucleotide", "oligonucleotide" and "nucleotide sequence" are used interchangeably and refer to a deoxyribonucleotide and/or ribonucleotide molecule. The nucleotide sequence may be single- or double-stranded. The nucleic acid may be prepared by conventional techniques. In particular, the nucleic acid may be prepared by, e.g., recombinant, enzymatic and/or chemical techniques, and subsequently replicated in a host cell or an in vitro system. The nucleotide sequence preferentially comprises an open reading frame encoding a (poly)peptide. The nucleotide sequence may contain additional sequences such as a transcription terminator, a signal peptide, an intron, etc.

As used herein, the term "active part", when relating to a nucleotide or polypeptide sequence, refers to a part of the sequence which retains an activity. In relation to binding domains (such as cellulose-binding domains, cohesin domains, or SLH domains), an "active part" refers to any segment of the domain that retains the ability to bind the target molecule. An active part typically comprises more than 10 consecutive amino acids of the reference domain.

As used herein, the term "polypeptide" refers to any chain of amino acids linked by peptide bonds, regardless of length or post-translational modification. Polypeptides include natural proteins, synthetic or recombinant polypeptides and peptides (i.e., polypeptides of less than 50 amino acids).

As used herein, the term "amino acid" refers to the 20 standard alpha-amino acids as well as naturally occurring and synthetic derivatives. A polypeptide may contain L or D amino acids or a combination thereof.

The term "genetic engineering" is used to refer to a process by which genetic materials, including DNA and/or RNA, are manipulated in a cell or introduced into a cell to affect expression of certain proteins in said cell. Such a modified cell may be called a "recombinant cell".

A "recombinant bacterium" refers to a bacterium whose genome contains at least one inserted nucleic acid sequence. Typically, the inserted nucleic acid is not naturally present in the genome of the bacterium. The nucleic acid sequence may be assembled and/or inserted in said bacterium or an ancestor thereof using recombinant DNA technology. The nucleic acid may be integrated into the chromosome, or present on a plasmid.

Within the context of the invention, the term "derived from a microorganism" in relation to an enzyme or (poly) peptide indicates that the enzyme or (poly)peptide has been isolated from such a microorganism, or that the enzyme or (poly)peptide comprises all or a biologically active part of the amino acid sequence of an enzyme or (poly)peptide isolated or characterized from such a microorganism.

The term "vector" refers to a DNA or RNA molecule used as a vehicle to transfer recombinant genetic material into a host cell. The major types of vectors are plasmids, bacteriophages, viruses, cosmids, and artificial chromosomes. The vector itself is generally a DNA sequence that comprises an insert (a nucleic acid sequence, transgene) and a sequence that serves as the "backbone" of the vector. The purpose of a vector is typically to isolate, transfer, clone, multiply, or express an insert in a target host cell. Vectors called expression vectors (expression constructs) are specifically adapted for the expression of the inserted sequences in the target cell, and generally have a promoter sequence that drives expression of the inserted sequence. Further regulatory elements may be present in an expression vector such as a ribosome binding site, a terminator, and optionally an operator. Preferably, an expression vector also contains an origin of replication for autonomous replication in a host cell, and/or a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. Bacterial expression vectors well known in the art include pET11a (Novagen), lambda gt11 (Invitrogen).

Expression vectors may be introduced into host cells using standard techniques. Examples of such techniques include transformation, transfection, lipotransfection, protoplast fusion, and electroporation. Examples of techniques for introducing nucleic acid into a cell and expressing the nucleic acid to produce protein are provided in references such as Ausubel, Current Protocols in Molecular Biology, John Wiley, 1987-1998, and Sambrook et al., Molecular Cloning: A Laboratory Manual, $2^{nd}$ Edition, Cold Spring Harbor Laboratory Press, 1989.

Recombinant Scaffolding Polypeptide

The inventors have developed and synthesized novel scaffolding polypeptides with efficient activity. More particularly, the inventors have conceived and produced various scaffolding polypeptides with new combinations of functional domains, allowing binding to cellulosomal and/or non-cellulosomal enzymes, attachment to cell wall, and binding to cellulose. These novel scaffolding polypeptides can be produced recombinantly and introduced into bacteria. The scaffolding polypeptides of the invention may comprise synthetic or naturally-occurring functional domains linked together, directly or using linker sequences. The domains may be derived from natural scaffolding proteins from various species or bacteria such as CbpA, which is from *Clostridium cellulovorans* cellulosome (Doi and Tamaru, 2001 Chem Rec. 1(1):24-32).

CbpA is a large protein of about 170 kDa that consists essentially of a signal peptide, a Cellulose Binding Domain (CBD), nine cohesin domains (which bind cellulosomal enzymatic subunit dockerin domains), and four S-layer Homology (SLH) Domains.

In a particular embodiment, the scaffolding polypeptide of the invention comprises a CBD, an SLH domain, and from 2 to 8 cohesin domains, preferably from 2 to 7, from 2 to 6, even more preferably 2, 3, 4, 5 or 6.

In another preferred embodiment, the mini-scaffolding polypeptide comprises (i) a CBD, (ii) from 1 to 5 SLH domains, preferably 1, 2, 4 or 5, and (iii) from 2 to 8 cohesin domains, preferably from 2 to 7 or from 2 to 6, even more preferably 2, 3, 4, 5 or 6.

In a particular and preferred example, the polypeptide of the invention contains one CBD, one SLH and 2 cohesin domains, and no further binding domains. Such a scaffolding protein can anchor two cellulosomal enzymes through the cohesins. An example of such a scaffolding polypeptide comprises the signal peptide, the CBD, the first SLH domain and the cohesins 1 and 2 of cbpA (SEQ ID NO: 2).

In another particular and preferred example, the polypeptide of the invention contains one CBD, 4 SLH and 3 cohesin domains, and no further binding domains. Such a scaffolding protein can anchor three cellulosomal enzymes through the cohesins. An example of such a scaffolding polypeptide comprises the signal peptide, the CBD, the first 2 SLH domains, the cohesins 1 and 2, the last 2 SLH domains and the cohesin domain 9 of cbpA (SEQ ID NO: 42).

In another particular and preferred example, the polypeptide of the invention contains one CBD, 5 SLH and 2 cohesin domains, and no further binding domains. Such a scaffolding protein can anchor 2 cellulosomal enzymes through the cohesins. An example of such a scaffolding polypeptide comprises the signal peptide, the CBD, the first 2 SLH domains and the cohesins 1 and 2 of cbpA, linked to the 3 SLH domains of EngE (SEQ ID NO: 43).

The polypeptide generally further comprises a signal peptide, allowing secretion of the polypeptide. Upon secretion, the signal peptide may be cleaved from the polypeptide. In an embodiment, the signal peptide is or is derived from the signal peptide of cbpA (SEQ ID NO: 21). Alternatively, the signal peptide may be a different signal peptide, such as the signal peptide of L. lactis protein Usp45 of sequence SEQ ID NO: 45, or any other natural or synthetic signal peptide functional in a bacterium.

In an embodiment, the sequence of the signal peptide comprises all or an active part of SEQ ID NO: 21 or 45, the sequence of the Cellulose Binding Domain comprises all or an active part of SEQ ID NO: 22, the sequences of the cohesin domains independently comprise all or an active part of any one of SEQ ID NOS: 3 to 11, and the sequences of the SLH domains independently comprise all or an active part of at least one of SEQ ID NOS: 12 to 15 and SEQ ID NOS: 35 to 37.

In a further embodiment, the polynucleotide according to the invention, corresponding to a truncated form of the cbpA gene, comprises parts of the cbpA gene that encode for the original signal peptide, the CBD, one SLH domain chosen among the 4 SLH domains, and two cohesins chosen among the nine cohesin domains.

More generally, other polypeptides capable of serving as scaffolding proteins for the assembly of cellulosomes and sharing at least about 70% sequence identity with the polypeptide or domains disclosed above may be used as well. More preferably, polypeptides of the invention include polypeptides having a sequence of, or comprising a domain having at least 80%, 90%, 95%, 98% or 99% sequence identity with the above domains or sequences.

In a particular embodiment, the polynucleotide encoding the scaffolding protein further comprises at least an additional nucleotide sequence encoding one or several additional cohesins, for anchoring one or several additional cellulosomal enzymes. Advantageously, said nucleotide sequence comprises all or an active part of at least a nucleotide sequence as set forth in any one of SEQ ID NO: 3 to SEQ ID NO: 11.

The scaffolding polypeptide can further comprise at least one additional SLH domain, for enhancing attachment of the resulting polypeptide to the wall of a host cell expressing said polypeptide. Advantageously, said nucleotide sequence comprises all or an active part of a nucleotide sequence as set forth in any one of SEQ ID NO: 12 to SEQ ID NO: 15.

The additional SLH domains may also be SLH domains of an enzyme which is anchored to the scaffolding protein, preferably an endoglucanase, in particular EngE. The sequence of the three SLH domains of EngE is set forth in SEQ ID NOS: 35 to 37. In a particular embodiment, said at least one additional SLH domain is selected from any one of the SLH domains provided in SEQ ID N° 35 to 37.

A further object of the invention is a polynucleotide encoding a scaffolding polypeptide as defined above.

The invention further relates to a vector, such as a plasmid, comprising a polynucleotide encoding a scaffolding protein, as described above. Preferentially, the vector further comprises regulatory elements (e.g., promoter(s)) allowing expression of the polynucleotide in a host cell. As discussed above, the vector may be a plasmid, phage, episome, artificial chromosome or the like. The vector may be produced by methods known in the art.

Recombinant Cellulosome Complex

The recombinant scaffolding polypeptide of the invention can be used together with dedicated cellulosomal enzymes, which can anchor the recombinant scaffolding polypeptide through cohesins and eventually additional non-cellulosomal enzyme(s).

Advantageously, the cellulosomal enzymes are chosen from endoglucanase and exoglucanase derived from Clostridium cellulovorans. More particularly, C. cellulovorans expresses at least nine cellulosomal cellulases: EngB, EngE, EngH, EngK, EngL, EngM, EngY, EngZ, and ExgS (Jeon et al., N. Biotechnol., 2012 Feb. 15, 29(3):365-71; Murashima et al., J Bacteriol., 2002 September, 184(18): 5088-95), which may be used for building the recombinant cellulosome of the invention.

Preferentially, the recombinant cellulosome complex contains at least one of the endoglucanase chosen among EngE, EngH and EngZ, and the exoglucanase ExgS.

Advantageously, the number of cohesins of the recombinant scaffolding polypeptide is adapted to the number of cellulosomal enzymes which have to be anchored.

In order to degrade crystalline cellulose to glucose, an additional enzyme, i.e., β-glycosidase, must be provided. Such β-glycosidase does not naturally anchor to the cellulosome complex but cooperates synergistically with the endoglucanase and exoglucanase for degrading crystalline cellulose. In an embodiment, the β-glycosidase is a recombinant β-glycosidase. For instance, a recombinant β-glycosidase comprising a dockerin domain, which is able to anchor the recombinant scaffolding polypeptide, can be included in the recombinant cellulosome. The sequence of the dockerin domain preferably comprises all or an active part of the nucleotide sequences as set forth in any one of SEQ ID NO: 38 to SEQ ID NO: 41.

It is therefore an object of the invention to propose a vector, such as an expression vector, containing, in addition to the isolated polynucleotide encoding the truncated scaffolding protein, a nucleotide sequence encoding an endoglucanase suitable for binding the recombinant scaffolding protein through a cohesin domain and/or a nucleotide sequence encoding an exoglucanase suitable for binding the recombinant scaffolding protein through a cohesin domain of said recombinant scaffolding protein.

Advantageously, the nucleotide sequence encoding the endoglucanase comprises all or an active part of a nucleotide sequence as set forth in any one of SEQ ID NO: 16 to SEQ ID NO: 18, corresponding respectively to the nucleotide sequences encoding EngE, EngH and EngZ.

Advantageously, the nucleotide sequence encoding the exoglucanase comprises all or an active part of a nucleotide sequence as set forth in SEQ ID NO: 19, corresponding to the nucleotide sequence encoding ExgS.

In the same way, the vector can comprise a nucleotide sequence encoding a β-glycosidase. Advantageously, the nucleotide sequence encoding the β-glycosidase comprises all or an active part of a nucleotide sequence as set forth in SEQ ID NO: 20, corresponding to the nucleotide sequence encoding an extracellular non-cellulosomal β-glucan glucohydrolase (BglA, 51.6 kDa) from *C. cellulovorans*. Such BglA acts in concert with cellulosomes to degrade cellulose to glucose (Kosugi et al., 2006, Biochem. Biophys. Res. Commun., 349(1):20-3). BglA is able to hydrolyze cellooligosaccharides ranging from cellobiose (G2) to cellotetraose (G4) and shows higher affinity for longer chain length oligosaccharides (i.e., cellotetraose) than for cellobiose (Kosugi et al., 2006, Biochem. Biophys. Res. Commun., 349 (1):20-3). BglA has high homology with β-glycosidase from several thermophilic bacteria such as *Thermoanaerobacter brockii*, *Caldicellulosiruptor saccharolyticus*, and *Thermotoga maritima* (55-56% identities) (Kosugi et al., 2006, Biochem. Biophys. Res. Commun., 349(1):20-3).

Recombinant Bacteria

The invention relates to recombinant bacteria which contain or express a recombinant cellulosome complex, preferably a polynucleotide or polypeptide as defined above. The invention indeed shows that it is possible to recombinantly create a functional cellulosome system in bacteria. The invention is particularly suitable and advantageous for expressing a recombinant cellulosome into a lactic acid bacterium.

As indicated above, lactic acid bacteria are any bacteria having the capacity to produce lactic acid. Examples of lactic acid bacteria include, without limitation, *Lactococcus* bacteria such as *Lactococcus lactis*, or *Lactobacillus* bacteria such as *Lactobacillus plantarum*, *Lactobacillus delbrueckii*, *Lactobacillus reuteri*, *Lactobacillus johnsonii*, *Lactobacillus gasseri*, or *Lactobacillus brevis*.

Further examples may be selected or identified by the skilled artisan using conventional techniques.

A particular object of the invention therefore relates to a recombinant bacterium comprising a recombinant polynucleotide encoding a scaffolding polypeptide of the invention.

In a particular embodiment, the bacterium further expresses cellulosomal enzymes and forms a functional cellulosome complex.

In a more preferred embodiment, the recombinant bacterium is a lactic acid bacterium.

The nucleic sequences encoding the recombinant scaffolding polypeptide and/or the cellulosomal enzymes (e.g., endoglucanase, exoglucanase and/or the β-glycosidase) may be introduced into the bacterium using vectors as described above. Several vectors, containing different polynucleotides, may be used for modifying the bacterium. For example, a first vector containing the polynucleotide encoding the recombinant scaffolding polypeptide is used together with one or several vectors containing the polynucleotides encoding the chosen cellulosomal and non-cellulosomal enzymes. Advantageously, the corresponding genes are stably incorporated into the genome of the bacterium.

More generally, the invention relates to a recombinant lactic acid bacterium, wherein said bacterium expresses a recombinant scaffolding polypeptide comprising at least a signal peptide, a Cellulose Binding Domain, two cohesin domains and an S-layer Homology domain, and optionally at least a recombinant endoglucanase suitable for binding the recombinant scaffolding protein through a cohesin domain, and/or at least a recombinant exoglucanase suitable for binding the recombinant scaffolding protein through another cohesin domain, and/or a recombinant β-glycosidase.

The recombinant lactic acid bacterium may comprise a polynucleotide as described above, encoding the recombinant scaffolding polypeptide and/or enzymes.

Advantageously, the recombinant bacterium further expresses and secretes several endoglucanases, and preferentially at least two endoglucanases among EngE, EngH and EngZ, preferably EngE and at least one of EngH and EngZ, suitable for anchoring the scaffolding polypeptide. In a particular embodiment, the recombinant lactic acid bacterium comprises all or an active part of a nucleotide sequence as set forth in any one of SEQ ID NO: 16 to SEQ ID NO: 18 encoding an endoglucanase.

In addition, the recombinant lactic acid bacterium of the invention may further comprise all or an active part of a nucleotide sequence as set forth in SEQ ID NO: 19 encoding the exoglucanase ExgS. The resulting bacterium expresses and secretes said exoglucanase suitable for anchoring the scaffolding polypeptide.

In addition, the recombinant lactic acid bacterium of the invention may comprise all or an active part of a nucleotide sequence as set forth in SEQ ID NO: 20 encoding a β-glycosidase. The resulting bacterium expresses and secretes said β-glycosidase.

Advantageously, the recombinant scaffolding polypeptide is attached to the cell wall of the recombinant lactic acid bacterium. The cellulosomal enzymes are excreted and anchored to the scaffolding polypeptide through the cohesins.

Otherwise, different lactic acid bacteria may be modified for expressing different parts of the cellulosome complex. More particularly, a first lactic acid bacterium may be modified for expressing a scaffolding polypeptide as described above, and one or several lactic acid bacteria may be modified for expressing and secreting the chosen cellulosomal and non-cellulosomal enzymes. Both the lactic acid bacterium expressing the scaffolding polypeptide and the bacteria expressing and excreting the cellulosomal and non-cellulosomal enzymes may be cultivated together so that the cellulosomal and non-cellulosomal enzymes, which are expressed and excreted by the second bacterium/bacteria, anchor the expressed scaffolding polypeptide on the wall of the first modified lactic acid bacterium. The corresponding co-culture is able to degrade cellulosic biomass and to produce lactic acid from said cellulosic biomass.

Production of Lactic Acid

According to the invention, the recombinant lactic acid bacteria as described above may be used for modifying a cellulosic biomass to produce a product of interest, and more preferentially to produce lactic acid.

In this regard, an object of the invention relates to a method for degrading a cellulosic biomass using a recombinant bacterium of the invention.

A further object of the invention relates to a method for degrading a cellulosic biomass comprising:

a) exposing a cellulosic biomass to a recombinant bacterium of the invention, or an extract thereof comprising the scaffolding polypeptide; and
b) optionally collecting the resulting products.

The resulting products of the methods of the invention may comprise degradation products and/or fermentation products thereof. Preferably, the resulting products comprise, in particular consist of, fermentation products of the degradation products of the cellulosic biomass. When the bacterium is a lactic acid bacterium, a preferred fermentation product is lactic acid.

The above method is particularly adapted to produce lactic acid from a cellulosic biomass. In this regard, in an embodiment, the method comprises the steps of:
a) Contacting a cellulosic biomass with a recombinant lactic acid bacterium, or an extract thereof comprising the scaffolding polypeptide, in conditions suitable for culturing and/or growing said recombinant lactic acid bacterium; and optionally
b) Collecting the resulting products.

In a preferred embodiment, the method comprises the steps of:
a) Contacting the cellulosic biomass with a recombinant lactic acid bacterium expressing a scaffolding polypeptide, at least one endoglucanase, at least one exoglucanase and a β-glycosidase in conditions suitable for culturing and/or growing said recombinant lactic acid bacterium;
b) Culturing said recombinant lactic acid bacterium for degrading the cellulosic biomass; and
c) Optionally collecting the resulting products, and preferentially the resulting lactic acid.

In another embodiment, the method consists of a co-culture comprising the steps of:
a") Contacting the cellulosic biomass with a co-culture of recombinant bacteria, at least one recombinant lactic acid bacterium expressing a scaffolding polypeptide, and one or several recombinant bacteria expressing at least one endoglucanase and/or at least one exoglucanase and/or a β-glycosidase;
b") maintaining the co-culture; and optionally
c") collecting the resulting lactic acid.

The method may be performed in fermentors, in the field, or in any suitable device or container. The method may include the continuous injection of culture medium or enzymes and/or the regular collection of the produced products, particularly lactic acid.

Further aspects of the invention are disclosed in the following experimental section.

EXPERIMENTATIONS

Materials and Methods

Bacterial Strains

*C. cellulovorans* 743B (DSM 3052, DMSZ, Germany) is a strictly anaerobic, mesophilic, spore-forming bacterium isolated by Sleat et al. (1984, Appl. Environ. Microbiol., 48, 88-93) from a poplar wood anaerobic digester. It is among the most efficient cellulolytic organisms isolated so far. It was grown at 30° C. in the anaerobic medium described by Sleat et al. (1984, Appl. Environ. Microbiol., 48, 88-93).

*Echerichia coli* TOP10 (Invitrogen) [F⁻ mcrA Δ(mrr-hsdRMS-mcrBC) φ80lacZ ΔlacX74 recA1 araD139 Δ(ara-leu) 7697 galU galK rpsL (Str$^R$) endA1 nupG] was used as the intermediate host for the gene cloning strategy. It has been routinely grown in Luria-Bertani medium at 37° C. with shaking (180 rpm).

*Lactococcus lactis* IL1403 was used as the recipient strain for the metabolic engineering strategy. It is a plasmid-free, easy-to-transform strain deriving from cheese starter strain IL594 (Johansen, 2003, Genet. Mol. Res., 2, 112-6). It is a model organism for molecular studies, and both its genome and proteome have been extensively characterized (Bolotin et al., 2001, Genome Res., 11, 731-53; Guillot et al., 2003, Proteomics, 3(3):337-54.). It is a homofermentative strain, producing mainly L(+)-LA. For routine cultures it has been grown at 30° C. in M17 medium (Terzaghi and Sandine, 1975, Appl Microbiol., 29(6):807-13) supplemented with 0.5% glucose.

*C. Cellulovorans* gDNA Extraction

*Clostridium cellulovorans* was grown on the medium described by Sleat et al. (1984, Appl. Environ. Microbiol., 48, 88-93) supplemented with 5 g/l cellobiose. Cells were then collected by centrifugation (16,000×g, 10', room temperature) and resuspended in 379 μl SET buffer (50 mM Tris-HCl pH 7.5, 67 g/l sucrose, 1 mM EDTA) supplemented with 20 mg/ml lysozyme and 97 μl 25 mM Tris-HCl pH 7.5. After 5 minutes of incubation at room temperature, the suspension was supplemented with 48 μl 50 mM Tris-HCl pH 8, 0.25 mM EDTA and 28 μl 50 mM Tris-HCl pH 8, EDTA 10 mM, 20% w/v SDS. Two extractions have then been performed: the former with phenol:chloroform:isoamyl alcohol (25:24:1), the latter with chloroform. gDNA was then precipitated with 50 μl 0.3 M sodium acetate and 1 ml 96% ethanol. Finally, the pellet was washed with 70% ethanol and resuspended in 50 μl of TE buffer (10 mM Tris-HCl pH 7.5 supplemented with 1 mM EDTA pH 8).

pMG36e Vector Optimization: Construction of pMG36eaΔ

An *E. coli-L. lactis* shuttle vector was used for *C. cellulovorans* gene cloning and expression in *L. lactis* IL1403; this vector was developed by optimizing the pMG36e vector that was constructed by van de Guchte et al. (1989, Appl. Environ. Microbiol., 55, 224-228) and supplied was by Prof. Jan Kok of the University of Groningen (the Netherlands). pMG36e was chosen because it allows gene cloning under the control of the constitutive p32 lactococcal promoter.

The pMG36e vector harbours a single selection marker, i.e., an erythromycin resistance gene (van de Guchte et al., 1989, Appl. Environ. Microbiol., 55, 224-228). Selection of *E. coli* transformants harbouring the plasmids of interest could not be performed since *E. coli* TOP10 was resistant to erythromycin up to 500 μg/ml. A second selection marker was then introduced into the pMG36e vector, by cloning the ampicillin resistance cassette from pUC19 (Invitrogen). The 1110 bp region, including the bla promoter, the bla encoding gene and the terminator sequence, was amplified, by using the amp-D and amp-R primers (Table I—SEQ ID NOS: 25 and 26), and inserted into the unique NheI site of pMG36e, thus obtaining the plasmid pMG36ea.

As well as its parent vector pMG36e, the pMG36ea vector is a translational fusion vector. Actually, it contains a translation start signal (ATG codon) downstream of the p32 Ribosome Binding Site (RBS). The multiple cloning site (MCS) is positioned 31 nt downstream of the ATG codon. Inserts are then cloned in frame and merged to the signal peptide encoding sequence of the existing open reading frame (ORF). Gene products are then biosynthesized as cytosolic fusion proteins. In order to clone the genes of interest with a suitable signal peptide for gene product secretion, the pMG36ea vector was further modified so as to delete the 34 bp fragment that is comprised between the pMG36ea ATG codon (including the ATG codon itself) and the SacI site of the MCS. For this purpose, pMG36ea was amplified by using ΔATG-D and ΔATG-R primers (Table I—SEQ ID NOS: 23 and 24). PCR products were digested by SacI and ligated by T4 DNA ligase. By this strategy the pMG36eaΔ was obtained. Alternatively, pMG36ea was amplified by using ΔXhoI-D and ΔXhoI-R primers (Table I—SEQ ID NOS: 46 and 47). By this strategy a new XhoI site which was absent in pMG36ea was inserted upstream of SacI, thus allowing the modified vector to be distinguished from the original one. PCR products were digested with XhoI and ligated by T4 DNA ligase. By this strategy the pMG36eaΔX was obtained.

C. Cellulovorans Gene Cloning into pMG36eaΔ bglA encodes an extracellular non-cellulosomal β-glucan glucohydrolase (BglA, 51.6 kDa) from *C. cellulovorans*, which acts in concert with cellulosomes to degrade cellulose to glucose (Kosugi et al., 2006, Biochem. Biophys. Res. Commun. 349, 20-23).

engD (1548 bp) encodes an extracellular non-cellulosomal endoglucanase (EngD, 56 kDa) from *C. cellulovorans*, which is active on both cellulose, xylan, mannan and lichenan (Foong and Doi, 1992, J. Bacteriol., 174, 1403-9; Doi et al., 1998, Extremophiles, 2, 53-60). EngD consists of a signal peptide, a catalytic domain that is connected through a Pro/Thr rich domain to a Cellulose Binding Domain (CBD).

cbpA encodes the main scaffolding protein (CbpA) of the *C. cellulovorans* cellulosome (Doi and Tamaru, 2001, Chem Rec., 1(1):24-32).

bglA and engD were amplified from the gDNA of *C. cellulovorans* by PCR using the high fidelity and processivity Phusion DNA polymerase (Finnzymes). Primer pairs bglA-D/bglA-R and engD-D/engD-R were designed in order to amplify full-length bglA and engD, respectively, including their original signal peptide encoding sequences (Kosugi et al., 2006, Biochem. Biophys. Res. Commun., 349, 20-23; Hamamoto et al., 1992, Mol. Gen. Genet., 231(3):472-9) (Table I—SEQ ID NOS: 27 to 30). To promote directional cloning of PCR products in respect to the p32 promoter, the consensus sequences for SacI and XbaI were included in the bglA-D and bglA-R primers, respectively, and the consensus sequences for SacI and SphI were included in the engD-D and engD-R primers, respectively. By cloning bglA into pMG36eaΔ the pΔB plasmid was obtained. By cloning engD into pMG36eaΔ the pΔE plasmid was obtained.

mini-cbpA$_{2C}$ and minicbpA$_{2C}$HT. mini-cbpA$_{2C}$ (SEQ ID NO: 2) consists of the first 1734 bp of the cbpA gene that encode the original signal peptide, the CBD, the first SLH domain and the cohesins 1 and 2. It was amplified from the gDNA of *C. cellulovorans* by using the cbpA-D and mcbpA2C-R primers (Table I—SEQ ID NOS: 32 and 33). A mini-cbpA2C version (minicbpA$_{2C}$HT) encoding for the mini-CbpA$_{2C}$ protein with a 6× His tag at the C-terminus was also amplified from the gDNA of *C. cellulovorans* by using the cbpA-D and mcbpA2CHT R primers (Table I—SEQ ID NOS: 33 and 34). Both mini-cbpA2C and mini-cbpA2CHT were cloned into the pMG36eaΔ vector between the unique SacI and XbaI restriction sites, thus obtaining the pΔmC2C and pΔmC2CH vectors.

r-cbpA$_{SLH4}$ and r-cbpA$_{SLH4}$HT: r-cbpA$_{SLH4}$ (SEQ ID NO: 42) was obtained by fusing the first 2001 bp of cbpA (Fragment 1), which encode the original signal peptide, the CBD, the SLH domains 1 and 2, and the cohesins 1 and 2, with the 987 bp positioned at the 3' of the same gene (Fragment 2) and encoding the SLH domains 3 and 4 and cohesin domain 9: r-cbpA$_{SLH4}$ consists therefore of 2988 bp encoding the original signal peptide, the CBD, 3 cohesins (1, 2, 9) and all the SLH domains of CbpA scaffoldin. Fragment 1 and 2 were separately amplified from the gDNA of *C. cellulovorans* using the cbpA-D and cbpA$_{SLH4}$-R1 primers for Fragment 1, and the cbpA$_{SLH4}$-D2 and cbpA-R primers for Fragment 2 (Table I—SEQ ID NOS: 49 and 50). Fragment 1 and 2 were then fused by PCR amplification by using a mixture of the PCR products obtained from the first amplification as the templates together with the cbpA-D and cbpA-R primers. A r-cbpA$_{SLH4}$ version (r-cbpA$_{SLH4}$HT) encoding for the r-CbpA$_{SLH4}$ protein with a 6× His tag at the C-terminus was constructed as described above, by replacing the cbpA-R primer with the cbpA-RH primer (Table I—SEQ ID NO: 51). Both r-cbpA$_{SLH4}$ and r-cbpA$_{SLH4}$HT were cloned in the pCR4-Blunt-TOPO vector (Invitrogen), thus obtaining the pTC$_{SLH4}$ and pTC$_{SLH4}$H vectors, respectively.

r-cbpA$_{SLHE}$ (SEQ ID NO: 43). It is a sequence of 3567 bp that consists of Fragment 1 of cbpA (see previous paragraph), joined at its 3' end with the fragment (i.e., Fragment E) comprised between by 94-1656 of engE (SEQ ID NOS: 35 to 37) and encoding the SLH domains 1, 2 and 3 of EngE. The strategy performed to obtain this construct was analogous to that used for the construction of r-cbpA$_{SLH4}$: Fragment 1 and Fragment E were separately amplified from the gDNA of *C. cellulovorans*, using the cbpA-D and cbpA$_{SLH4}$-R1 primers for Fragment 1 and the engESLH-D and engESLH-R2 primers for Fragment E (Table I—SEQ ID NOS: 32 and 48, SEQ ID NOS: 52 and 53). Fragment 1 and Fragment E were then fused by PCR using the cbpA-D and engESLH-R2 primers. r-cbpA$_{SLHE}$ was cloned in the pMG36eaΔ vector between the unique SacI and XbaI restriction sites, thus obtaining the pΔC$_{SLHE}$ vector.

Construction of the Artificial Bicistronic bglA-engD Operon

A fragment, containing the full-length sequence encoding *C. cellulovorans* EngD positioned downstream of the RBS$_{p32}$ sequence, was cloned into the pΔB plasmid downstream of bglA. engD was amplified from *C. cellulovorans* gDNA by using the engD-DRBS and engD-R primers (Table I—SEQ ID NOS: 30 and 31). The amplified fragment was cloned between the XbaI and SphI sites of the pΔB plasmid. By this strategy, the pΔBE plasmid was obtained. pΔBE contains the artificial bicistronic bglA-engD operon that is positioned under the control of the transcriptional promoter p32.

TABLE I

| Primer name | Sequence |
|---|---|
| ΔATG-D | 5' TTTTTT*GAGCTC*GCCCGGGGATCGATC 3' (SEQ ID NO: 23) |
| ΔATG-R | 5' TTTTTT*GAGCTC*TTCAAAATTCCTCCGAATATTT TTTTAC 3' (SEQ ID NO: 24) |
| ΔXho-D | 5' TTTTTT*CTCGAG*CTCGCCCGGGGATCG 3' (SEQ ID NO: 46) |
| ΔXho-R | 5' TTTTTT*CTCGAG*TTCAAAATTCCTCCGAATAATT TTTTTAC 3' (SEQ ID NO: 47) |
| ampD | 5' TTTTTT*GCTAGC*A<u>CCCCTATTTGTTTATTTTTCT AAATAC</u> 3' (SEQ ID NO: 25) |
| ampR | 5' TTTTTT*GCTAGC*<u>GTCTGACGCTCAGTGGAACGAA AAC</u> 3' (SEQ ID NO: 26) |
| bglA-D | 5' TTTTTT*GAGCTC*<u>ATGGAAAAGCTAAGATTTCCCA AAG</u> 3' (SEQ ID NO: 27) |
| bglA-R | 5' TTTTTT*CTAGA*<u>TTACTTATTAGATCTTTCTATAA GCTCC</u> 3' (SEQ ID NO: 28) |

TABLE I-continued

| Primer name | Sequence |
|---|---|
| engD-D | 5' TTTTTT*GAGCT*CATGATTAAACATCTATTATCAC GGGG 3' (SEQ ID NO: 29) |
| engD-R | 5' TTTTTT*GCATG*CTATTTTACTGTGCATTCAGTAC CATTC 3' (SEQ ID NO: 30) |
| engD-DRBS | 5' TTTTTT*TCTAGA*GGGTAGGTAAAAAAATATTCGGA GGAATTTTGAAATGATTAAACATCTATTATCACGGGG 3' (SEQ ID NO: 31) |
| cbpA-D | 5' TTTTTT*GAGCT*CATGCAAAAAAAGAAATCGCTGA ATTTATTG 3' (SEQ ID NO: 32) |
| mcbpA$_{2C}$-R | 5' TTTTT*TCTAGA*TTATTCTAGTATAGGATCTCCAA TATTTATTG 3' (SEQ ID NO: 33) |
| mcbpA$_{2C}$HT-R | 5' TTTTT*TCTAGA*TTAGTGATGATGATGATGATGTT CTAGTATAGGATCTCCAATATTTATTG 3' (SEQ ID NO: 34) |
| cbpA$_{SLH4}$-R1 | 5' AGTTTTTGGTGCATCTTTGATTGATAC 3' (SEQ ID NO: 48) |
| cbpA$_{SLH4}$-D2 | 5' GTATCAATCAAAGATGCACCAAAAACTACAGTAG CTCCAACAGCTGTAACATTTG 3' (SEQ ID NO: 49) |
| cbpA-R | 5' TTTTT*TCTAGA*TTAGCTAACTTTAACACTTCCGT TAAC 3' (SEQ ID NO: 50) |
| cbpA-RH | 5' TTTTT*TCTAGA*TTAGTGATGATGATGATGGC TAACTTTAACACTTCCGTTAACTG 3' (SEQ ID NO: 51) |
| engESLH-D | 5' 5'GTATCAATCAAAGATGCACCAAAAACTGCAGA AGCTAACTACACAACAAAAG 3' (SEQ ID NO: 52) |
| engESLH-R2 | 5' TTTTT*TCTAGA*TTATAAATCCATAGCAGAAAGAC CTCTC 3' (SEQ ID NO: 53) |

Transformation of *E. coli* TOP10

All constructions were obtained and transformed into RbCl$_2$ chemocompetent *E. coli* TOP10. *E. coli* TOP10 cells containing the plasmid of interest were selected by plating them on LB agar medium supplemented with 100 µg/ml ampicillin.

Transformants were analysed by plasmid minipreparation according to the alkaline lysis method (Qiaprep Miniprep, Qiagen; GeneElute HP Plasmid Midiprep Kit, Sigma Aldrich) and restriction profile analysis and/or by colony PCR and sequencing (MWG Operon, Germany).

Transformation of *L. lactis* IL1403

Constructions were extracted and purified from *E. coli* by the alkaline lysis method (GeneElute HP Plasmid Midiprep Kit, Sigma Aldrich) and transformed into electrocompetent *L. lactis* IL103 cells. For preparation of electrocompetent *L. lactis* cells, the protocol of Gerber and Solioz (2007, J. Basic. Microbiol., 47, 281-6) was used. Aliquots of electrocompetent *L. lactis* cells were transformed with about 1 µg of plasmid DNA by electroporation. For electroporation, 0.2 cm gap electroporation cuvettes were used (BioRad) and a 2.45 kV electric field was applied using a MicroPulser (BioRad). Cells harbouring the plasmids of interest were selected by plating them on SR agar+5 µg/ml erythromycin and incubating them for 24-48 h at 30° C. (Gerber and Solioz, 2007, J. Basic. Microbiol., 47, 281-6).

To very quickly screen a large number of transformants, small amounts of cells were analyzed directly by PCR. Plasmids were then isolated from *L. lactis* positive clones with the Qiagen miniprep kit adapted to include lysozyme (5 mg/ml) in the resuspension buffer to facilitate cell degradation (Hanniffy et al., 2009, Appl. Environ. Microbiol., 75(8): 2326-32) and then analyzed by restriction profile analysis.

Characterization of Recombinant *L. lactis* Strains: Analysis of Heterologous Gene Expression and Gene Product Activity Recombinant *L. lactis* cells were grown over-night in 100 ml GM17 medium supplemented with 5 µg/ml erythromycin at 30° C. without shaking.

Biomass was separated from culture broth by centrifugation (3005×g, 15', 4° C.). Biomass was washed twice in 1 mM EDTA 50 mM Tris-HCl pH 7.3, resuspended in the same buffer and disrupted by ultrasonic treatment, keeping the samples on ice. Crude extracts were centrifuged (3005× g, 15', 4° C.) to separate unbroken cells and membrane fragments, and supernatants (cellular extracts) were kept for further analyses.

Heterologous Gene Expression Analysis: Cellulose Binding Assay

This assay is able to isolate and detect proteins that are able to strongly bind cellulose from complex mixtures, e.g., proteins that contain a CBD. Among the proteins in the study, mini-CbpA$_{2C}$, mini-CbpA$_{2C}$HT, and EngD contain a CBD, while BglA does not.

Both cell-free culture broths (100 ml) and cellular extracts (10 ml) were incubated 1 h at 25° C. with 0.8 g crystalline cellulose (Sigmacell, Sigma) with slight horizontal shaking. Samples were then centrifuged (3000×g, 15', 4° C.). Pellets, consisting of crystalline cellulose and cellulose-bound proteins, were washed twice with 50 mM potassium phosphate buffer pH 6.0 (3000×g, 15', 4° C.), then resuspended in 750 µl of loading buffer for SDS-PAGE. Samples were incubated 10 minutes at 95° C., so as to promote cellulose-bound protein solubilisation, and centrifuged (16,000×g, 5', 4° C.).

Proteins in supernatants were quantified by the 2D quant kit (GE Healthcare), which is suitable for detergent (e.g., SDS) containing protein samples, and also by using bovine serum albumin (BSA) as the standard.

Furthermore, supernatants analysed by SDS-PAGE by using 10% polyacrylamide gels. After migration, gels were stained with R-250 Coomassie Brilliant Blue.

Heterologous Gene Product Activity Analysis

Cell free culture broths (100 ml) of the recombinant *L. lactis* strains were 100 fold concentrated by using Vivaspin ultrafiltration devices (Sartorius Stedim) with 30 kDa cut-off. Concentrated extracellular extracts were used for enzyme activity assays.

β-Glycosidase Activity Assay

The β-glycosidase activity was measured by the absorbance of liberated p-nitrophenol from p-nitrophenyl-β-D-glucopyranoside (pNGP), at 410 nm (Kosugi et al, 2006, Biochem. Biophys. Res. Commun., 349, 20-23). Assay mixtures containing 1 mM pNGP in 50 mM sodium phosphate buffer (pH 6.0) were incubated for 30 min at 37° C., and the reactions were stopped by addition of Na$_2$CO$_3$. One unit of the activity toward p-nitrophenol derivatives was defined as the amount of enzyme liberating 1 µmol of p-nitrophenyl/min.

Characterization of Recombinant *L. lactis* Strains: Analysis of Cellulose Degradation Cellulose Hydrolysis Assay Carboxymethylcellulase (CMCase) activity of the recombinant *L. lactis* strain was analysed by the Congo Red method (Teather and Wood, 1982, Appl. Environ. Microbiol., 43:777-780). Briefly, cells were plated on GM17 medium supplemented with 0.2% CMC and incubated at 30° C. for 72 h to enable microbial growth and enzyme expression. Then cells were washed away from each plate with deionized water and the plates were then flooded with 0.1% Congo Red (Sigma) for 1 h at room temperature in slight agitation. The Congo Red solution was then poured off and the plates were further treated by flooding with 1M NaCl. Finally, 1M HCl was used to shift the dye color from red to blue, and enhance CMC clearing halo detection.

Results

Construction of the pMG36eaΔ Vector

The *E. coli-L. lactis* pMG36e shuttle vector was conceived for the intracellular expression of genes fused with an existent N-terminal encoding sequence under the control of the constitutive p32 lactococcal promoter (Van de Guchte et al., 1989, Appl. Environ. Microbiol., 55, 224-228). Previous studies reported that the selection of *E. coli* transformants harbouring the pMG36 vector could be obtained by 100 μg/ml erythromycin pressure (Van de Guchte et al., 1989, Appl. Environ. Microbiol., 55, 224-228). However, in the study we demonstrated that *E. coli* TOP10, the strain used as intermediate host for the gene cloning strategy, is resistant up to 500 μg/ml erythromycin. In the present study, the pMG36e shuttle vector was modified for both: 1) easier *E. coli* transformant selection (i.e., by the addiction of a supplementary selection marker, that is, an ampicillin resistance cassette); and 2) the expression of genes containing a signal peptide-encoding sequence for their secretion in the extracellular medium.

The ampicillin resistance cassette (1116 bp), consisting of the beta-lactamase encoding gene, the bla promoter and a 144 bp fragment that contains a transcriptional terminator, from the pUC19 vector was amplified by PCR and cloned into the unique NheI site of the pMG36e vector, thus obtaining the pMG36ea vector.

The pMG36ea vector was amplified by using the ΔATG-D/ΔATG-R or XhoI-D/XhoI-R primer pair (Table I), digested respectively by SacI or XhoI, and ligated. By this strategy the pMG36eaΔ vector, lacking a 34 bp fragment comprised between the Ribosome Binding Site (RBS) and the multiple cloning site (MCS) of pMG36ea, and the pMG36eaΔX vector, lacking a 34 bp fragment comprised between the Ribosome Binding Site (RBS) and the multiple cloning site (MCS) of pMG36ea, but possessing the additional XhoI site at the 5' of MCS, were obtained. These vectors allow the cloning of genes, with their original signal peptide encoding sequences, at an optimized distance downstream of the $RBS_{p32}$.

Construction of Engineered Scaffolding Proteins

The genes encoding different engineered scaffolding proteins, consisting of the original signal peptide (SP) and the cellulose binding domain (CBD) of CbpA and different combinations of cohesin and S-layer homology (SLH) domains, were constructed:

mini-cbpA$_{2C}$ and minicbpA$_{2C}$HT mini-cbpA$_{2C}$ (SEQ ID NO: 2) consists of the first 1734 bp of the cbpA gene that encode the original SP, the CBD, the first SLH domain and the cohesins 1 and 2. minicbpA$_{2C}$HT encodes a mini-CbpA$_{2C}$ protein with a 6× His tag at the C-terminus. mini-cbpA$_{2C}$ and minicbpA$_{2C}$HT were amplified from the gDNA of *C. cellulovorans* and cloned in the pMG36eaΔ vector as previously described, thus obtaining the pΔmC2C and pΔmC2CH vectors. The pΔmC2C and pΔmC2CH vectors were first transformed into *E. coli*. Then these constructions were extracted and purified from *E. coli* and transformed into *L. lactis* IL1403 by electroporation, thus obtaining *L. lactis* (pΔmC2C) and *L. lactis* (pΔmC2CH), respectively.

r-cbpA$_{SLH4}$ and r-cbpA$_{SLH4}$HT. r-cbpA$_{SLH4}$ (2988 bp, SEQ ID NO: 42) was obtained by fusing the first 2001 bp of cbpA (Fragment 1), which encode the original signal peptide, the CBD, the SLH domains 1 and 2, and the cohesins 1 and 2, with the 987 bp positioned at the 3' of the same gene (Fragment 2) and encodes the SLH domains 3 and 4 and the cohesin domain 9, as previously described. r-cbpA$_{SLH4}$HT encoding a r-CbpA$_{SLH4}$ protein with a 6× His tag at the C-terminus. Both r-cbpA$_{SLH4}$ and r-cbpA$_{SLH4}$HT were cloned in the pCR4-Blunt-TOPO vector, thus obtaining the pTC$_{SLH4}$ and pTC$_{SLH4}$H vectors, respectively, and transformed in *E. coli*.

r-cbpA-I. By fusing Fragment1 and 2 of cbpA using the primers cbpA-D and cbpA-RH (Table I) as described in the Materials and Methods section, a further fusion PCR product of 2069 bp, that is, r-cbpA-I (SEQ. ID NO: 44), was obtained. r-cbpA-I was cloned in the pCR4-Blunt-TOPO vector, thus obtaining the pTC$_I$ vector, and transformed in *E. coli*. Nucleotide sequencing showed that r-cbpA-I encodes a protein consisting of the SP, CBD, SLH 1 and 2, and cohesin 1 and 2 of CbpA followed by five isoleucines.

r-cbpA$_{SLHE}$ (3567 bp, SEQ ID NO: 43) was obtained by fusing Fragment 1 of cbpA (see previous paragraph) with Fragment E, comprised between by 94-1656 of engE, which encodes the SLH domains 1, 2 and 3 of endoglucanase EngE, as previously described. r-cbpA$_{SLHE}$ was cloned in the pMG36eaΔ plasmid, thus obtaining the pΔC$_{SLHE}$ vector, and transformed in *E. coli*.

Cloning of *C. cellulovorans* bglA, engD, and Construction of an Artificial bglA-engD Operon into the pMG36eaΔ Vector and Transformation into *L. lactis* IL1403

The bglA, and engD genes were amplified from the *Clostridium* cellulovorans gDNA and individually cloned into the pMG36eaΔ vector as previously described, thus obtaining the pΔB and pΔE plasmids, respectively. The pΔBE plasmid, containing the bglA-engD artificial operon, was constructed by cloning the fragment containing the RBSp32 and the engD sequence in the pΔB vector downstream of bglA, as previously described.

All constructions were transformed into *E. coli*. pΔB, pΔE, and pΔBE plasmids were then extracted and purified from *E. coli* and transformed into *L. lactis* IL1403 by electroporation, thus obtaining *L. lactis* (pΔB), *L. lactis* (pΔE), and *L. lactis* (pΔBE), respectively.

*L. lactis* (pΔE) showed very inefficient growth in both liquid and agar-supplemented media, so, it was not possible to perform further characterization analyses on this strain so far. For these analyses, *L. lactis* (pΔE) was replaced by *L. lactis* (pBE). The pBE plasmid was constructed as follows: bglA was amplified from *C. cellulovorans* gDNA by using the bglA-D and bglA-R primers (Table I) and cloned into the pMG36ea vector, thus obtaining the pB vector. engD was amplified by using the engD-DRBS and engD-R primers (Table I) and cloned into the pB vector, thus obtaining the pBE vector. The pBE vector therefore has an identical sequence to the pΔBE, with the exception that the latter lacks the 34 bp fragment comprised between the Ribosome Binding Site (RBS) and the multiple cloning site (MCS) of pMG36ea. For this reason, even if pBE contains the bglA-engD artificial operon, only engD can be efficiently translated. From a metabolic standpoint, *L. lactis* (pBE) is therefore equivalent to *L. lactis* (pΔE). *L. lactis* (pBE) will therefore identified as *L. lactis* (pΔE)* in the following sections.

Characterization of Recombinant *L. lactis* Strains: Analysis of Heterologous Gene Expression and Gene Product Activity Heterologous Protein Biosynthesis in Recombinant *L. lactis*

The biosynthesis of *C. cellulovorans* EngD, mini-CbpA$_{2C}$ and mini-CbpA$_{2C}$HT in recombinant *L. lactis* strains was analyzed in both extracellular and total cellular protein fractions by cellulose binding assay followed by SDS-PAGE.

Analyses detected a band of about 56 kDa corresponding to EngD in the extracellular extracts of both *L. lactis* (pΔE)* and *L. lactis* (pΔBE), while the same band was not present in the cellular fraction of *L. lactis* (pΔE)* or *L. lactis* (pΔBE) (FIG. 1). These results showed that EngD is biosynthesized and efficiently secreted in both *L. lactis* (pΔE)* and *L. lactis* (pΔBE).

Furthermore, analyses showed a band of about 60 kDa, corresponding to mini-CbpA$_{2C}$, and 61 kDa, corresponding to mini-CbpA$_{2C}$HT, in extracellular fractions of *L. lactis* (pΔmC2C), and *L. lactis* (pΔmC2CH), respectively (FIG. 1). These results proved that mini-CbpA$_{2C}$ and mini-CbpA$_{2C}$HT were efficiently expressed and secreted by *L. lactis* (pΔmC2C) and *L. lactis* (pΔmC2CH), respectively.

Heterologous proteins represent almost the total of cellulose-bound proteins that were detected in the extracellular fractions of recombinant *L. lactis*. Quantitation of cellulose-bound proteins in these fractions is therefore a reliable measure of the amount of heterologous protein that is secreted by recombinant *L. lactis*. Analyses showed that about 1.1 µg of EngD, 3.7 µg of mini-CbpA$_{2C}$ and 2.1 µg of mini-CbpA$_{2C}$HT were secreted per mg (dry weight) of recombinant *L. lactis*.

Figure 2:
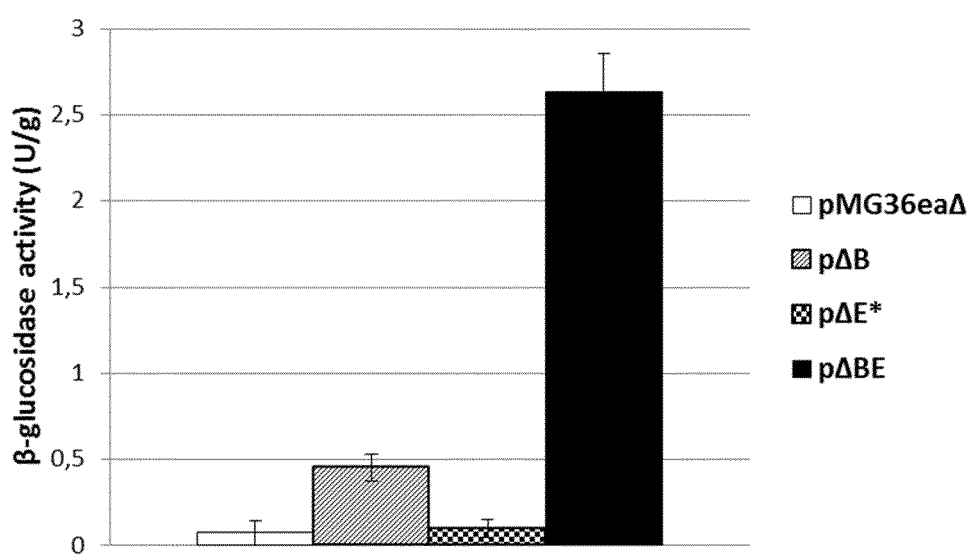
FIG. 2. β-glycosidase activity measured in the extracellular fraction of *L. lactis* (pMG36eaΔ), *L. lactis* (pΔB), *L. lactis* (pΔE)*, and *L. lactis* (pΔBE). Values are expressed as enzyme units (U) per g (dry weight) of biomass.

Heterologous Protein Activity in Recombinant *L. lactis*

β-Glycosidase Activity

β-glycosidase activity has been reported for both *C. cellulovorans* BglA and EngD (Foong and Doi, 1992, J. Bacteriol., 174, 1403-9; Kosugi et al., 2006, Biochem. Biophys. Res. Commun., 349, 20-23). β-glycosidase was tested in the extracellular medium of recombinant *L. lactis*. Results are shown in FIG. 2. Actually, the *L. lactis* (pΔB) extracellular protein fraction showed β-glycosidase activity that was significantly higher than control strain *L. lactis* (pMG36eaΔ), while β-glycosidase activity measured in *L. lactis* (pΔE)* was comparable to *L. lactis* (pMG36eaΔ). Surprisingly, β-glycosidase activity in *L. lactis* (pΔBE) was more than 5-fold higher than in *L. lactis* (pΔB). Since both bglA and engD are expressed under the same promoter and RBS, it is likely that their level of expression is the same in the different recombinant *L. lactis* strains constructed. The observed results suggest a possible synergism between BglA and EngD, thus enhancing β-glycosidase activity in *L. lactis* (pΔBE).

Characterization of Recombinant *L. lactis* Strains: CMCase Activity Assay

Figure 3:
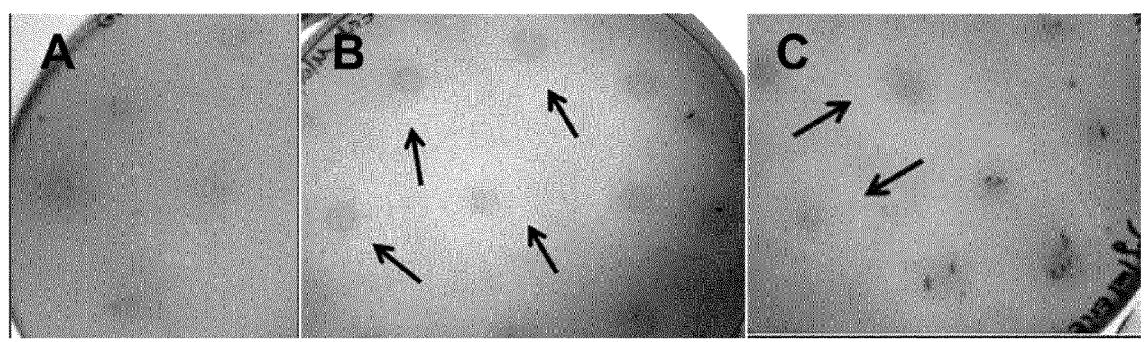
FIG. 3. CMCase activity assays performed on *L. lactis* (pΔB) (A), *L. lactis* (pΔE)* (B) and *L. lactis* (pΔBE) (C). Arrows indicate clearing halos that correspond to CMCase activity.

Recombinant *L. lactis* were plated on M17 medium supplemented with 0.2% CMC. Clearing halos, corresponding to CMC hydrolysis zones, were detected around *L. lactis* (pΔE)* and *L. lactis* (pΔBE) colonies, while no CMCase activity was detected for *L. lactis* (pMG36eaΔ) or *L. lactis* (pΔB) (FIG. 3).

CONCLUSIONS

Our results show that:

The *C. cellulovorans* bglA and engD can be individually cloned into the pMG36eaΔ vector, thus obtaining the pΔB and pΔE plasmids, respectively. Furthermore an artificial bglA-engD operon was constructed and cloned into the pMG36eaΔ vector, thus obtaining the pΔBE plasmid. The bglA-engD operon was also cloned into the pMG36ea vector, thus obtaining the pΔE* plasmid.

Three engineered forms of *C. cellulovorans* cbpA, that are r-cbpA$_{SLH4}$, r-cbpA$_{SLH4}$HT and r-cbpA-I, were individually cloned in the pCR4-Blunt-TOPO vector, thus obtaining the pTC$_{SLH4}$, pTC$_{SLH4}$H and the pTC$_I$ vectors, respectively.

A further engineered form of *C. cellulovorans* cbpA, that is, r-cbpA$_{SLHE}$, was cloned in the pMG36eaΔ plasmid, thus obtaining the pΔC$_{SLHE}$ vector.

Two further engineered forms of *C. cellulovorans* cbpA, that are mini-cbpA$_{2C}$ and mini-cbpA$_{2C}$HT, were individually cloned into the pMG36eaΔ vector, thus obtaining the pΔmC2C and pΔmC2CH vectors, respectively.

The pMG36eaΔ, pΔB, pΔE, pΔE*, pΔBE, pΔmC2C and pΔmC2CH vectors were transformed into *L. lactis* IL1403, thus obtaining *L. lactis* (pMG36eaΔ), *L. lactis* (pΔB), *L. lactis* (pΔE), *L. lactis* (pΔE)*, *L. lactis* (pΔBE), *L. lactis* (pΔmC2C) and *L. lactis* (pΔmC2CH).

*L. lactis* (pΔmC2C) and *L. lactis* (pΔmC2CH) biosynthesize and secrete mini-CbpA$_{2C}$ and mini-CbpA$_{2C}$HT in the extracellular medium.

*L. lactis* (pΔE)* and *L. lactis* (pΔBE) biosynthesize and secrete EngD in the extracellular medium. Furthermore, they both show CMCase activity, indicating that EngD is secreted in functional conformation.

*L. lactis* (pΔB) and *L. lactis* (pΔBE) biosynthesize and secrete an active form of BglA as indicated by β-glycosidase activity detected in their extracellular protein fractions.

In conclusion, the following polynucleotides were obtained:

polynucleotides comprising a signal peptide, a Cellulose Binding Domain, two cohesin domains and a SLH domain (mini-cbpa$_{2C}$, minicbpA$_{2C}$HT);

a polynucleotide comprising a signal peptide, a Cellulose Binding Domain, two cohesin domains and two SLH domains (r-cbpA-I);

polynucleotides comprising a signal peptide, a Cellulose Binding Domain, 3 cohesin domains and 4 SLH domains (r-cbpA$_{SLH4}$, r-cbpA$_{SLH4}$HT); and polynucleotides comprising a signal peptide, a Cellulose Binding Domain, 2 cohesin domains and 5 SLH domains, wherein 3 SLH domains are SLH domains of EngE (r-cbpA$_{SLHE}$).

Vectors comprising r-cbpA$_{SLH4}$, r-cbpA$_{SLH4}$HT, r-cbpA-I, r-cbpA$_{SLHE}$, mini-cbpA$_{2C}$ and mini-cbpA$_{2C}$HT were obtained. Bacteria transformed with each of the 6 vectors were obtained.

```
                                    SEQ ID NO: 2: mini-CbpA
ATGCAAAAAAGAAATCGCTGAATTTATTGTTAGCATTAATGATGGTATT

TGCTTTAGTACTACCAAGTATACCAGCTTTAGCAGCGACATCATCAATGT

CAGTTGAATTTTACAACTCTAACAAATCAGCACAAACAAACTCAATTACA

CCAATAATCAAAATTACTAACACATCTGACAGTGATTTAAATTTAAATGA

CGTAAAAGTTAGATATTATTACACAAGTGATGGTACACAAGGACAAACTT

TCTGGTGTGACCATGCTGGTGCATTATTAGGAAATAGCTATGTTGATAAC

ACTAGCAAAGTGACAGCAAACTTCGTTAAAGAAACAGCAAGCCCAACATC
```

-continued
```
AACCTATGATACATATGTTGAATTTGGATTTGCAAGCGGAGCAGCTACTC
TTAAAAAAGGACAATTTATAACTATTCAAGGAAGAATAACAAAATCAGAC
TGGTCAAACTACACTCAAACAAATGACTATTCATTTGATGCAAGTAGTTC
AACACCAGTTGTAAATCCAAAAGTTACAGGATATATAGGTGGAGCTAAAG
TACTTGGTACAGCACCAGGTCCAGATGTACCATCTTCAATAATTAATCCT
ACTTCTGCAACATTTGATAAAAATGTAACTAAACAAGCAGATGTTAAAAC
TACTATGACTTTAAATGGTAACACATTTAAAACAATTACAGATGCAAACG
GTACAGCTCTAAATGCAAGCACTGATTATAGTGTTTCTGGAAATGATGTA
ACAATAAGCAAAGCTTATTTAGCAAAACAATCAGTAGGAACAACTACATT
AAACTTTAACTTTAGTGCAGGAAATCCTCAAAAATTAGTAATTACAGTAG
TTGACACACCAGTTGAAGCTGTAACAGCTACAATTGGAAAAGTACAAGTA
AATGCTGGAGAAACGGTAGCAGTACCAGTTAACTTAACAAAAGTTCCAGC
AGCTGGTTTAGCAACAATTGAATTACCATTAACTTTTGATTCTGCATCAT
TAGAAGTAGTATCAATAACTGCTGGAGATATCGTATTAAATCCATCAGTA
AACTTCTCTTCTACAGTAAGTGGAAGCACAATAAAATTATTATTCTTAG
ATGATACATTAGGAAGCCAATTAATCACTAAGGATGGAGTTTTTGCAACA
ATAACATTTAAAGCAAAAGCTATAACTGGAACAACTGCAAAAGTAACTTC
AGTTAAATTAGCTGGAACACCAGTAGTTGGTGATGCGCAATTACAAGAAA
AACCTTGTGCAGTTAACCCAGGAACAGTAACTATCAATCCAATCGATAAT
AGAATGCAAATTTCAGTTGGAACAGCAACAGTAAAAGCTGGAGAAATAGC
AGCAGTGCCAGTAACATTAACAAGTGTTCCATCAACTGGAATAGCAACTG
CTGAAGCACAAGTAAGTTTTGATGCAACATTATTAGAAGTAGCATCAGTA
ACTGCTGGAGATATCGTATTAAATCCAACAGTAAACTTCTCTTATACAGT
AAACGGAAATGTAATAAAATTATTATTCCTAGATGATACATTAGGAAGCC
AATTAATTAGTAAAGATGGAGTTTTTGTAACAATAAACTTCAAAGCAAAA
GCTGTAACAAGCACAGTAACAACACCAGTTACAGTATCAGGAACACCTGT
ATTTGCAGATGGTACATTAGCAGAAGTACAATCTAAAACAGCAGCAGGTA
GCGTTACAATAAATATTGGAGATCCTATACTAGAATAA
```
SEQ ID NO: 42: r-cbpA$_{SLH4}$
```
ATGCAAAAAAGAAATCGCTGAATTTATTGTTAGCATTAATGATGGTATT
TGCTTTAGTACTACCAAGTATACCAGCTTTAGCAGCGACATCATCAATGT
CAGTTGAATTTACAACTCTAAACAAATCAGCACAAACAAACTCAATTACA
CCAATAATCAAAATTACTAACACATCTGACAGTGATTTAAATTTAAATGA
CGTAAAAGTTAGATATTATTACACAAGTGATGGTACACAAGGACAAACTT
TCTGGTGTGACCATGCTGGTGCATTATTAGGAAATAGCTATGTTGATAAC
ACTAGCAAAGTGACAGCAAACTTCGTTAAAGAAACAGCAAGCCCAACATC
AACCTATGATACATATGTTGAATTTGGATTTGCAAGCGGACGAGCTACTC
TTAAAAAAGGACAATTTATAACTATTCAAGGAAGAATAACAAAATCAGAC
TGGTCAAACTACACTCAAACAAATGACTATTCATTTGATGCAAGTAGTTC
AACACCAGTTGTAAATCCAAAAGTTACAGGATATATAGGTGGAGCTAAAG
TACTTGGTACAGCACCAGGTCCAGATGTACCATCTTCAATAATTAATC
```
-continued
```
CTACTTCTGCAACATTTGATAAAAATGTAACTAAACAAGCAGATGTTAA
AACTACTATGACTTTAAATGGTAACACATTTAAAACAATTACAGATGCA
AACGGTACAGCTCTAAATGCAAGCACTGATTATAGTGTTTCTGGAAATG
ATGTAACAATAAGCAAAGCTTATTTAGCAAAACAATCAGTAGGAACAAC
TACATTAAACTTTAACTTTAGTGCAGGAAATCCTCAAAAATTAGTAATT
ACAGTAGTTGACACACCAGTTGAAGCTGTAACAGCTACAATTGGAAAAG
TACAAGTAAATGCTGGAGAAACGGTAGCAGTACCAGTTAACTTAACAAA
AGTTCCAGCAGCTGGTTTAGCAACAATTGAATTACCATTAACTTTTGAT
TCTGCATCATTAGAAGTAGTATCAATAACTGCTGGAGATATCGTATTAA
ATCCATCAGTAAACTTCTCTTCTACAGTAAGTGGAAGCACAATAAAATT
ATTATTCTTAGATGATACATTAGGAAGCCAATTAATCACTAAGGATGGA
GTTTTTGCAACAATAACATTTAAAGCAAAAGCTATAACTGGAACAACTG
CAAAAGTAACTTCAGTTAAATTAGCTGGAACACCAGTAGTTGGTGATGC
GCAATTACAAGAAAAACCTTGTGCAGTTAACCCAGGAACAGTAACTATC
AATCCAATCGATAATAGAATGCAAATTTCAGTTGGAACAGCAACAGTAA
AAGCTGGAGAAATAGCAGCAGTGCCAGTAACATTAACAAGTGTTCCATC
AACTGGAATAGCAACTGCTGAAGCACAAGTAAGTTTTGATGCAACATTA
TTAGAAGTAGCATCAGTAACTGCTGGAGATATCGTATTAAATCCAACAG
TAAACTTCTCTTATACAGTAAACGGAAATGTAATAAAATTATTATTCCT
AGATGATACATTAGGAAGCCAATTAATTAGTAAAGATGGAGTTTTTGTA
ACAATAAACTTCAAAGCAAAAGCTGTAACAAGCACAGTAACAACACCAG
TTACAGTATCAGGAACACCTGTATTTGCAGATGGTACATTAGCAGAAGTA
CAATCTAAAACAGCAGCAGGTAGCGTTACAATAAATATTGGAGATCCTAT
ACTAGAACCAACAATAAGCCCTGTAACTGCAACTTTTGATAAAAAGCAC
CAGCAGACGTTGCAACAACAATGACATTAAATGGTTATACATTTAACGGA
ATCACAGGATTAACAACATCAGACTACAGTATTTCAGGTAATGTAGTGAA
TAATTAGCCAAGCATATTTAGCTAAACAACCAGTTGGAGATCTACATTAA
CATTTAACTTCTCAAATGGTAATAAAACTGCAACAGCTAAATTAGTAGTA
TCAATCAAAGATGCACCAAAAACTACAGTAGCTCCAACAGCTGTAACATT
TGATAAAGCTAATCAAGCAGATGCTGCAATAACAATGACATTAAACGGAA
ACACATTCTCAGCAATAAAGAATGGAACAGCTACATTAGTAAAAGGAACT
GATTACACAGTTTCAGAAAATGTAGTAACAATCAGCAAAGCTTACTTAGC
TAAGCAAACTGGAACAGTTACATTAGAATTTGTATTTGACAAAGGAAATT
CAGCTAAAGTTGTTGTAGCTGTAAAAGAAATTCAAATTGTAAATTCAACA
ATAACTCCAGTAGTAGCAACATTTGAAAAAACTGCTGCTAAACAAGCAGA
TGTTGTAGTAACAATGTCTTTAAATGGTAACACATTCTCAGCAATAAAGA
ATGGAACAACTACATTAGTAAAAGGAACTGATTACACAATTTCAGGAAGC
ACAGTAACAATCAGCAAAGCTTACCTAGCTACATTAGCAGATGGAAGTGC
AACATTAGAATTTGTATTTAACCAAGGGGCTAGTGCAAAATTACGATTAA
CTATAGTACCAGCAGTAGTAGATCCAGTAGTAACTGATTTTGCTGTTAA
AATTGACAAAGTATCTGCAGCAGCAGGTTCTACAGTTAAAGTTCCAGTAT
```

-continued

CATTAATTAATGTTTCTAAGGTTGGAAATGTTTGTGTAGCTGAATACAAA
ATCAGCTTTGACTCAAGTGTACTTACATATGTAGGAACTACAGCAGGAAC
ATCAATCAAAATCCTGCAGTTAACTTCTCATCACAACTTAACGGAAACA
CTATTACATTATTATTCTTTGACAATACAATTGGAAATGAATTAATAACA
GCTGATGGTCAATTCGCTACAATCGAATTCAAAGTTAATGCAGCAGCTAC
TTCAGGAACAACTGCAGAAGTTAAAGTAGCAACTATAAGCTCATTCGCTG
ATGCATCATTAACTGAAATCACTAAAGTAGCTACAGTTAACGGAAGTGTT
AAAGTTAGCTAA

SEQ ID NO: 43: r-cbpA$_{SLHE}$
ATGCAAAAAAGAAATCGCTGAATTTATTGTTAGCATTAATGATGGTATT
TGCTTTAGTACTACCAAGTATACCAGCTTTAGCAGCGACATCATCAATGT
CAGTTGAATTTTACAACTCTAACAAATCAGCACAAACAAACTCAATTACA
CCAATAATCAAAATTACTAACACATCTGACAGTGATTTAAATTTAAATGA
CGTAAAAGTTAGATATTATTACACAAGTGATGGTACACAAGGACAAACTT
TCTGGTGTGACCATGCTGGTGCATTATTAGGAAATAGCTATGTTGATAAC
ACTAGCAAAGTGACAGCAAACTTCGTTAAAGAAACAGCAAGCCCAACATC
AACCTATGATACATATGTTGAATTTGGATTTGCAAGCGGACGAGCTACTC
TTAAAAAAGGACAATTTATAACTATTCAAGGAAGAATAACAAAATCAGAC
TGGTCAAACTACACTCAAACAAATGACTATTCATTTGATGCAAGTAGTTC
AACACCAGTTGTAAATCCAAAAGTTACAGGATATATAGGTGGAGCTAAA
GTACTTGGTACAGCACCAGGTCCAGATGTACCATCTTCAATAATTAATCC
TACTTCTGCAACATTTGATAAAAATGTAACTAAACAAGCAGATGTTAAAA
CTACTATGACTTTAAATGGTAACACATTTAAAACAATTACAGATGCAAAC
GGTACAGCTCTAAATGCAAGCACTGATTATAGTGTTTCTGGAAATGATGT
AACAATAAGCAAAGCTTATTTAGCAAAACAATCAGTAGGAACAACTACAT
TAAACTTTAACTTTAGTGCAGGAAATCCTCAAAAATTAGTAATTACAGTA
GTTGACACACCAGTTGAAGCTGTAACAGCTACAATTGGAAAAGTACAAGT
AAATGCTGGAGAAACGGTAGCAGTACCAGTTAACTTAACAAAAGTTCCAG
CAGCTGGTTTAGCAACAATTGAATTACCATTAACTTTTGATTCTGCATCA
TTAGAAGTAGTATCAATAACTGCTGGAGATATCGTATTAAATCCATCAGT
AAACTTCTCTTCTACAGTAAGTGGAAGCACAATAAAATTATTATTCTTAG
ATGATACATTAGGAAGCCAATTAATCACTAAGGATGGAGTTTTTGCAACA
ATAACATTTAAAGCAAAAGCTATAACTGGAACAACTGCAAAAGTAACTTC
AGTTAAATTAGCTGGAACACCAGTAGTTGGTGATGCGCAATTACAAGAAA
AACCTTGTGCAGTTAACCCAGGAACAGTAACTATCAATCCAATCGATAAT
AGAATGCAAATTTCAGTTGGAACAGCAACAGTAAAAGCTGGAGAAATAGC
AGCAGTGCCAGTAACATTAACAAGTGTTCCATCAACTGGAATAGCAACTG
CTGAAGCACAAGTAAGTTTTGATGCAACATTATTAGAAGTAGCATCAGTA
ACTGCTGGAGATATCGTATTAAATCCAACAGTAAACTTCTCTTATACAGT
AAACGGAAATGTAATAAAATTATTATTCCTAGATGATACATTAGGAAGCC
AATTAATTAGTAAAGATGGAGTTTTTGTAACAATAAACTTCAAAGCAAAA GCTGTAACAAGCACAGTAACAACACCAGTTACAGTATCAGGAACACCTGT
ATTTGCAGATGGTACATTAGCAGAAGTACAATCTAAAACAGCAGCAGGTA
GCGTTACAATAAATATTGGAGATCCTATACTAGAACCAACAATAAGCCCT
GTAACTGCAACTTTTGATAAAAAAGCACCCAGCAGACGTTGCAACAACAAT
GACATTAAATGGTTATACATTTAACGGAATCACAGGATTAACAACATCAG
ACTACAGTATTTCAGGTAATGTAGTGAAAATTAGCCAAGCATATTTAGCT
AAACAACCAGTTGGAGATCTTACATTAACATTTAACTTCTCAAATGGTAA
TAAAACTGCAACAGCTAAATTAGTAGTATCAATCAAAGATGCACCAAAAA
CTGCAGAAGCTAACTACACAACAAAAGGCACTACGACACAGATATATCTT
AGTGCCTTTGCACAAAATACTGATGACTGGGCTTGGATGAGTATGGGAGA
TACTGCTAGCTTAGTATATCAAGACGTAACAAATTTCAATGCCATCGACG
CTACTAGTGCCTTTGCAAAGGCAAATGGTACTGCAAACTTTGGGTTACAG
GTTGTTGATGGAAATCTTGCTGCAGGAGAAAAAGTACATTAAAATTCCA
TATTGGAACAGTTACTATTAAAGCAACTGGATATAATGATGTTGTGGTTA
ATCTTAACAAGGATTATTCAGAAGCATATGCAGCAGAAAAGTTTCTTGG
GGAATCACAGGAAACAATACATCAATTTTACTAAATGATTATTTACCAAC
AGATGCAGCAGCGAAAGCAACGTATCTACAAAAGATTACTAGTGTAAAAG
CAGATGTTACATTATCAGAATATCAATTTGTTAAACCAGCATCAACTGGG
TCAACTTCTGAAAGTGTATACTCATCAGGTGATGCAACAAAGATTTATGC
TAGTGCGTTTGCACAAAATACTGATGACTGGGCTTGGATGAGCATGGGAG
ATACTGCTGTTTTAACATATCAAACTGCTACAAACGTAAATGCTATCAAT
GCAGGTACTGCATTTGCAAGTGCAAATGGAACTGCAAACTTTGGTATCCA
AATTGTTGACGGAAACCTAGCTGCTGCAGGAGACTCAAGTACATTAAAAT
TCCATGTTGGAACAGTTACAATTAAAGCAACAGGTTATGATGATCTTGTA
GTTGCTCTAAATAAAGATTATTCAGAAGCATATACTGCAGAAAAAATGAC
TTGGGGACTTACTGGAAATAACACACAAATTTTATTAAATAGTTATTTAC
CAACGGATGCAACTGCAAAAGCTGCATATCTACAAAAAATAACTTCTGTT
ACAGCTGATGTTACAGTAACAGATTATCAATCGATTAAACCAGCAACAGC
AACTGGGGAAGTTCTTTACACAACACCAGGTGTTGAAACAAAGATTTCTG
CTAGTGCTTTTGCACAAAACACCGATGACTGGGCTTGGATGAGCGTAGGT
GATGGTGTTAGTCTTCAATATCAAACTGATACAACTTTAAATGCTATTAG
TGCTGCTGGTACATTAGCAAAAGCAAATGCTACAGCAAACTTTGGTATAA
ATATTGTTGATGGAAATCTTGCTGCTGGAGATGCAAACACATTAAAGTTC
CATGTTGGAACAGTTACAATTAAAGCAACAGGTTATGATGACCTTGTGAT
TAACTTAAATAAAGATTACTCAGAAGCATTTGCAGCAGAAAAAGCTTCTT
GGGGACTTACAGGAAACACAAAACAAATTTTATTAAACTCTTATTTACCA
ACAGATGCAACAGCAAAAGTAAACTATCTTCAAAAGGTTACTAGTGTTAC
AGCTGATGTAAAAGTAACAGATTATACGTTTATTAAAATATGTACCACCAG
CACCAGAATTCCCTGCTGATTACACTCACCCAACAGAAATGAGAGGTCTT
TCTGCTATGGATTTATAA

The invention claimed is:

1. An isolated polynucleotide encoding a recombinant scaffolding polypeptide comprising a signal peptide, a Cellulose Binding Domain, one or more S-layer Homology (SLH) domains and from 2 to 8 cohesin domains,
   wherein the sequence of the signal peptide comprises SEQ ID NO: 21 or 45, the sequence of the Cellulose Binding Domain comprises SEQ ID NO: 22, the sequences of the cohesin domains independently comprise any one of SEQ ID NOs: 3 to 11, and the sequences of the SLH domains independently comprise any one of SEQ ID NOs: 12 to 15 and 35 to 37.

2. The isolated polynucleotide of claim 1, wherein said isolated polynucleotide comprises the nucleotide sequence as set forth in SEQ ID NO: 42 or 43.

3. A vector comprising a polynucleotide of claim 1.

4. The vector of claim 3, further comprising a nucleotide sequence encoding a cellulosomal enzyme selected from an endoglucanase or an exoglucanase that binds the recombinant scaffolding protein through a cohesin domain.

5. The vector of claim 4, wherein the endoglucanase is encoded by a sequence comprising a nucleotide sequence as set forth in any one of SEQ ID NOs: 16 to 18 and the exoglucanase is encoded by a sequence comprising SEQ ID NO: 19.

6. The vector of claim 3, further comprising a nucleotide sequence encoding a β-glycosidase.

7. A recombinant bacterium transformed with or containing a polynucleotide of claim 1.

8. A recombinant bacterium, wherein said bacterium expresses a recombinant scaffolding protein encoded by the polynucleotide of claim 1, and further expresses:
   at least a recombinant endoglucanase that binds to the recombinant scaffolding protein through a cohesin domain thereof,
   at least a recombinant exoglucanase that binds to the recombinant scaffolding protein through another cohesin domain thereof, and/or
   a recombinant β-glycosidase.

9. The recombinant bacterium of claim 8, wherein said bacterium is a lactic acid bacterium.

10. A fermentation tank comprising a cellulosic biomass and the recombinant lactic acid bacterium of claim 9.

* * * * *

UNITED STATES PATENT AND TRADEMARK OFFICE
CERTIFICATE OF CORRECTION

PATENT NO. : 9,528,132 B2
APPLICATION NO. : 14/405504
DATED : December 27, 2016
INVENTOR(S) : Roberto Mazzoli et al.

It is certified that error appears in the above-identified patent and that said Letters Patent is hereby corrected as shown below:

In the Specification

Column 8,
Line 28, "cellulovorans." should read --*cellulovorans*.--.

Column 13,
Line 59, "r-cbpA$_{SLH4}$HT:" should read --r-cbpA$_{SLH4}$HT.--.

Column 14,
Line 19, "between by" should read --between bp--.

Column 16,
Line 61, "of Cellulose Degradation Cellulose Hydrolysis Assay" should read
--of Cellulose Degradation
Cellulose Hydrolysis Assay--.

Column 17,
Line 55, "minicbpA$_{2C}$HT mini-cbpA$_{2C}$" should read --minicbpA$_{2C}$HT. mini-cbpA$_{2C}$--.

Column 18,
Line 25, "between by" should read --between bp--.
Line 34, "cellulovorans" should read --*cellulovorans*--.

Column 20,
Line 38, "(mini-cbpa$_{2C}$," should read --(mini-cbpA$_{2C}$,--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*